United States Patent
Socha et al.

(10) Patent No.: US 9,765,044 B2
(45) Date of Patent: Sep. 19, 2017

(54) SYNTHESIS OF NOVEL IONIC LIQUIDS FROM LIGNIN-DERIVED COMPOUNDS

(71) Applicants: THE REGENTS OF THE UNIVERSITY OF CALIFORNIA, Oakland, CA (US); SANDIA CORPORATION, Livermore, CA (US)

(72) Inventors: Aaron Socha, New York, NY (US); Seema Singh, Fremont, CA (US); Blake A. Simmons, San Francisco, CA (US); Maxime Bergeron, Quebec (CA)

(73) Assignees: The Regents of the University of California, Oakland, CA (US); Sandia Corporation, Livermore, CA (US)

( * ) Notice: Subject to any disclaimer, the term of this patent is extended or adjusted under 35 U.S.C. 154(b) by 0 days.

(21) Appl. No.: 14/776,454

(22) PCT Filed: Mar. 14, 2014

(86) PCT No.: PCT/US2014/028684
§ 371 (c)(1),
(2) Date: Sep. 14, 2015

(87) PCT Pub. No.: WO2014/172042
PCT Pub. Date: Oct. 23, 2014

(65) Prior Publication Data
US 2016/0031843 A1    Feb. 4, 2016

Related U.S. Application Data

(60) Provisional application No. 61/793,138, filed on Mar. 15, 2013.

(51) Int. Cl.
| | | |
|---|---|---|
| *A61K 31/34* | (2006.01) |
| *C07D 307/52* | (2006.01) |
| *C07C 209/00* | (2006.01) |
| *C07C 209/28* | (2006.01) |
| *C07C 213/02* | (2006.01) |
| *C07C 213/08* | (2006.01) |
| *C07C 215/66* | (2006.01) |
| *C07C 217/58* | (2006.01) |
| *C07D 295/03* | (2006.01) |
| *C07C 209/04* | (2006.01) |
| *C07C 211/63* | (2006.01) |
| *C08H 8/00* | (2010.01) |
| *C09K 3/00* | (2006.01) |
| *H01M 10/0569* | (2010.01) |
| *C12P 19/02* | (2006.01) |
| *C12P 19/14* | (2006.01) |

(52) U.S. Cl.
CPC .......... *C07D 307/52* (2013.01); *C07C 209/00* (2013.01); *C07C 209/04* (2013.01); *C07C 209/28* (2013.01); *C07C 211/63* (2013.01); *C07C 213/02* (2013.01); *C07C 213/08* (2013.01); *C07C 215/66* (2013.01); *C07C 217/58* (2013.01); *C07D 295/03* (2013.01); *C08H 8/00* (2013.01); *C09K 3/00* (2013.01); *H01M 10/0569* (2013.01); *C12P 19/02* (2013.01); *C12P 19/14* (2013.01); *H01M 2300/0037* (2013.01); *H01M 2300/0045* (2013.01)

(58) Field of Classification Search
CPC .................................................... C07D 307/52
See application file for complete search history.

(56) References Cited

U.S. PATENT DOCUMENTS

2008/0185112 A1* 8/2008 Argyropoulos ........ C07H 19/01
162/9

FOREIGN PATENT DOCUMENTS

DE    102006011077 A1    9/2007

OTHER PUBLICATIONS

International Search Report and Written Opinion dated Jul. 29, 2014 of International Patent Application No. PCT/US2014/028684, 10 pages.
Adbel-Magid et al., "Reductive Amination of Aldehydes and Ketones with Sodium Triacetoxyborohydride. Studies on Direct and Indirect Reductive Amination Procedures1", *J. Org. Chem*, 61(11):3849-3862 (1996).

\* cited by examiner

*Primary Examiner* — Rei-Tsang Shiao
(74) *Attorney, Agent, or Firm* — Kilpatrick Townsend & Stockton LLP

(57) ABSTRACT

Methods and compositions are provided for synthesizing ionic liquids from lignin derived compounds comprising: contacting a starting material comprising lignin with a depolymerization agent to depolymerize the lignin and form a mixture of aldehyde containing compounds; contacting the mixture of aldehyde containing compounds with an amine under conditions suitable to convert the mixture of aldehyde containing compounds to a mixture of amine containing compounds; and contacting the mixture of amine containing compounds with an acid under conditions suitable to form an ammonium salt, thereby preparing the ionic liquid.

12 Claims, 16 Drawing Sheets a) phenol to aniline b) phenol to aniline to IL

X : HSO₄⁻ or H₂PO₄⁻

SYNTHESIS OF NOVEL IONIC LIQUIDS FROM LIGNIN-DERIVED COMPOUNDS

CROSS-REFERENCES TO RELATED APPLICATIONS

This application is a National Stage of International Application No. PCT/US2014/028684, filed Mar. 14, 2014, and claims the benefit of priority to U.S. Provisional Application No. 61/793,138, filed Mar. 15, 2013, the contents of which are hereby incorporated by reference in the entirety for all purposes.

STATEMENT AS TO RIGHTS TO INVENTIONS MADE UNDER FEDERALLY SPONSORED RESEARCH AND DEVELOPMENT

The invention described and claimed herein was made utilizing funds supplied by the U.S. Department of Energy under Contract No. DE-AC02-05CH11231. The government has certain rights in this invention.

BACKGROUND OF THE INVENTION

Biorefineries process biological materials such as lignocellulosic biomass, or components derived therefrom, to extract and produce valuable materials. Lignin utilization is a key biorefinery concept, and efficient lignin utilization is important for improving the economic viability of biorefineries. Similarly, lignin can be obtained as a product of manufacturing pulp and paper from lignocellulosic biomass. Examples of lignins produced in the pulp and paper industry include kraft lignin, produced via the kraft process, lignosulfonates, produced, e.g. from the sulfite pulping process, alkali lignin, produced, e.g. from treating the black liquor from the soda process with acid, and low sulfonate alkali lignin. As with lignocellulosic biomass, these lignins may be further extracted, purified, and/or derivatized.

Often, the lignin from biorefiners and pulp and paper manufacturers is combusted to generate heat, steam, or electricity. This use of lignin provides minimal economic value as compared to other sources of heat, steam, or electricity such as natural gas. Further, new and more energy efficient plants can produce more lignin than they require for generation of heat, steam, and electricity. Thus, new technologies are needed to convert polymeric lignin produced by biorefiners and pulp or paper manufacturers into higher value products.

Lignocellulosic biomass is derived from agricultural wastes, forest residues and dedicated energy crops. In recent years, tremendous effort has been applied to develop methods for production of useful compounds from lignocellulosic biomass. However, one of the greatest limitations facing the economic viability of this technology is the recalcitrant nature of the lignocellulosic biomass, which resists breakdown and extraction of useful compounds. This resistance necessitates the use of treatment steps to enhance the accessibility to and depolymerization of the carbohydrate and lignin components present in the lignocellulosic biomass. Most treatment processes are comprised of thermo-chemical processes that utilize combinations of high temperatures and pressures, or dilute acids or alkalis, to open up the structure of the biomass. Such processes necessitate the use of specialized equipment and high-energy inputs.

Ionic liquids (ILs) recently emerged as innovative fluids for chemical processing. They are considered environmentally friendly solvents primarily due to their low volatility and their potential recyclability. Significantly, the use of ILs for the treatment of biomass has been shown to be a promising technology, allowing for the solubilization of crystalline cellulose from biomass under relatively mild conditions.

Although treatment of lignocellulosic biomass with ionic liquids has met with success, ionic liquids are expensive and the treatment process can be both energy and time intensive. As such, what is needed in the art is a process that produces lower cost ionic liquids and produces a supply of commercially useful, high-value, and renewable lignin-derived compounds to help improve overall process economics. The present invention provides compositions and methods that fulfill these and other needs.

BRIEF SUMMARY OF THE INVENTION

In some embodiments, the present invention provides a process for preparing an ionic liquid comprising: contacting a starting material comprising lignin with a depolymerization agent to depolymerize the lignin and form a mixture of aldehyde containing compounds; contacting the mixture of aldehyde containing compounds with an amine under conditions suitable to convert the mixture of aldehyde containing compounds to a mixture of amine containing compounds; and contacting the mixture of amine containing compounds with an acid under conditions suitable to form an ammonium salt, thereby preparing the ionic liquid.

In some embodiments, the present invention provides an ionic liquid prepared by contacting a starting material comprising lignin with a depolymerization agent to depolymerize the lignin and form a mixture of aldehyde containing compounds; contacting the mixture of aldehyde containing compounds with an amine under conditions suitable to convert the mixture of aldehyde containing compounds to a mixture of amine containing compounds; and contacting the mixture of amine containing compounds with a mineral acid under conditions suitable to form an ammonium salt, thereby preparing an ionic liquid.

In some embodiments, the present invention provides an ionic liquid comprising at least one compound of the following formula:

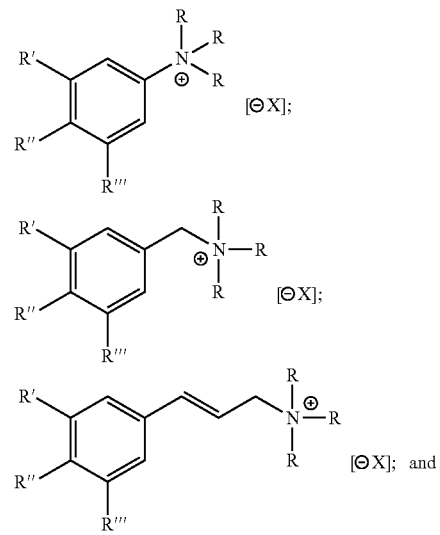

-continued

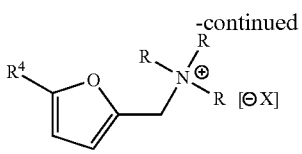

wherein each of the R groups of the nitrogen is H, CH$_3$, or CH$_2$CH$_3$; at least two of the R groups of the nitrogen are independently selected from CH$_3$, or CH$_2$CH$_3$; R', R", and R''' are independently selected from H, OH, and OCH$_3$; R$^4$ is selected from H, OH, and CH$_2$OH; and X is an acid anion.

In some embodiments, the present invention provides a mixture comprising at least two of the foregoing ionic liquids. In some cases, the present invention provides a mixture comprising at least three of the foregoing ionic liquids. In some cases, the present invention provides a mixture comprising at least four of the foregoing ionic liquids. In some cases, the present invention provides a mixture comprising at least five of the foregoing ionic liquids. In some cases, the present invention provides a mixture comprising at least six of the foregoing ionic liquids. In some cases, the present invention provides a mixture comprising at least seven of the foregoing ionic liquids. In some cases, the present invention provides a mixture comprising at least eight of the foregoing ionic liquids. In other cases, the present invention provides a mixture comprising at least nine of the foregoing ionic liquids. In some cases, the present invention provides a mixture comprising at least 10% w/v of at least one the foregoing ionic liquids.

DETAILED DESCRIPTION OF THE INVENTION

I. Overview

Figure 1:
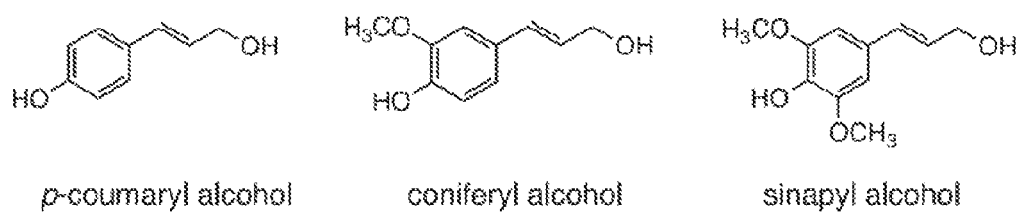
FIG. 1 depicts the three phenylpropane monomers present in all lignin.

Lignin, the second most abundant biopolymer on Earth, is a heterogeneous macromolecule comprised of the three phenylpropane units (a.k.a. monlignols) p-coumaryl alcohol, coniferyl alcohol and sinapyl alcohol. (FIG. 1) The monolignol composition of lignin varies as a function of its origin (hardwood, softwood or grass) and the method used for its extraction from biomass.

Lignin depolymerization includes methods such as pyrolysis (e.g., gasification, thermolysis, hydrogenolysis, hydrolysis), enzymatic depolymerization, chemical oxidation, combustion, and more recently ionic liquid-mediated depolymerization. Depending on the nature of the starting material (e.g., hardwood, softwood, or grass) and the extraction and depolymerization process, different product mixtures are obtained in various ratios (Pandey, (2011)).

Depolymerization can produce aromatic low molecular weight (e.g., monomer, dimer, trimer, etc.) products containing alcohol, aldehyde and carboxylic acid functional groups. These functional groups can serve as chemical "handles" upon which to convert lignin-derived monomers into ionic liquids. In some embodiments, the present invention provides ionic liquids derived from these low molecular weight (e.g., monomer, dimer, trimer, etc.) products of lignin depolymerization. For example, low molecular weight (e.g., monomer, dimer, trimer, etc.) products of lignin containing aldehydes, carboxylic acids, and alcohols can be converted by the methods of the present invention into ionic liquids. In some cases, one or more of the low molecular weight aldehydes, carboxylic acids, and alcohols are aromatic. In some cases, the ionic liquids are derived from a low cost starting material (e.g., lignin waste from a biorefiner, or a pulp or paper manufacturer). Thus ionic liquids of the present invention can be produced at a reduced cost. In some embodiments, the ionic liquids produced by the methods provided herein are novel. In some cases, mixtures of ionic liquids produced by the methods provided herein are novel mixtures.

Ionic liquids of the invention can be used for any methods known or contemplated for utilizing ionic liquids. For example, ionic liquids of the invention can be used for processing biomass, as a component of a battery electrolyte, as dispersants, in the manufacture of pharmaceuticals and commodity and fine chemicals, as a pharmaceutical agent, etc. In some embodiments, ionic liquids of the invention can be produced from lignin and utilized to extract, dissolve, and/or depolymerize lignin in concurrent or subsequent pretreatment steps. For example, the methods of the invention include a closed-loop process for generation of ionic liquids during a biomass treatment process for treatment of additional biomass.

II. Definitions

"Ionic liquid" refers to salts that are liquids rather than crystals at or near room temperature. It will be readily apparent to those of skill that numerous ionic liquids can be used in the methods of the present invention. Ionic liquids are taught in Chem Files (2006) 6(9) (which are commercially available from Sigma-Aldrich; Milwaukee, Wis.). Such ionic liquids include, but are not limited to, 1-alkyl-3-alkylimidazolium alkanoate, 1-alkyl-3-alkylimidazolium alkylsulfate, 1-alkyl-3-alkylimidazolium methylsulfonate, 1-alkyl-3-alkylimidazolium hydrogensulfate, 1-alkyl-3-alkylimidazolium thiocyanate, and 1-alkyl-3-alkylimidazolium halide, wherein an "alkyl" is an alkyl group comprising from 1 to 10 carbon atoms, and an "alkanoate" is an alkanoate comprising from 1 to 10 carbon atoms. In some cases, the alkyl is an alkyl group comprising from 1 to 4 carbon atoms. In some cases, the alkyl is a methyl group, ethyl group, propyl group, or butyl group. In some cases, the alkanoate is an alkanate comprising from 1 to 4 carbon atoms. In some embodiments, the alkanoate is an acetate. In some cases, the halide is chloride.

Exemplary ionic liquids include, but are not limited to 1-ethyl-3-methylimidazolium acetate (EMIM acetate) or ([C$_2$mim][OAc]), 1-ethyl-3-methylimidazolium chloride (EMIM Cl), 1-ethyl-3-methylimidazolium hydrogensulfate (EMIM HOSO$_3$), 1-ethyl-3-methylimidazolium methylsulfate (EMIM MeOSO$_3$), 1-ethyl-3-methylimidazolium ethylsulfate (EMIM EtOSO$_3$), 1-ethyl-3-methylimidazolium methanesulfonate (EMIM MeSO$_3$), 1-ethyl-3-methylimidazolium tetrachloroaluminate (EMIM AlCl4), 1-ethyl-3-methylimidazolium thiocyanate (EMIM SCN), 1-butyl-3-methylimidazolium acetate (BMIM acetate), 1-butyl-3-methylimidazolium chloride (BMIM Cl), 1-butyl-3-methylimidazolium hydrogensulfate (BMIM HOSO$_3$), 1-butyl-3-methylimidazolium methanesulfonate (BMIM MeSO$_3$), 1-butyl-3-methylimidazolium methylsulfate (BMIM MeOSO$_3$), 1-butyl-3-methylimidazolium tetrachloroaluminate (BMIM AlCl4), 1-butyl-3-methylimidazolium thiocyanate (BMIM SCN), 1-ethyl-2,3-dimethylimidazolium ethylsulfate (EDIM EtOSO$_3$), Tris(2-hydroxyethyl) methylammonium methylsulfate (MTEOA MeOSO$_3$), 1-methylimidazolium chloride (MIM Cl), 1-methylimidazolium hydrogensulfate (MIM HOSO$_3$), 1,2,4-trimethylpyrazolium methylsulfate, tributylmethylammonium methylsulfate, choline acetate, choline salicylate, and ionic liquids derived from low molecular weight lignin depolymerization products.

"Contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

"Lignin" is a phenylpropane polymer of monolignol monomers. It is generally found as an integral part of the secondary cell walls of plants and certain types of algae. There are three monolignol monomers, methoxylated to various degrees: p-coumaryl alcohol, coniferyl alcohol, and sinapyl alcohol. These lignols are incorporated into lignin in the form of the phenylpropanoids p-hydroxyphenyl (H), guaiacyl (G), and syringyl (S), respectively. Gymnosperms have a lignin that consists almost entirely of G with small quantities of H. That of dicotyledonous angiosperms is more often than not a mixture of G and S (with very little H), and monocotyledonous lignin is a mixture of all three. Many grasses have mostly G, while some palms have mainly S. All lignins contain small amounts of incomplete or modified monolignols, and other monomers are prominent in non-woody plants.

"Depolymerization agent" refers to any chemical or process for depolymerizing lignin. Exemplary depolymerization agents include CuSO$_4$/NaOH (Pearl, 1942), and the chemicals and processes provided in Pandey, 2011. Depolymerization agents can include ionic liquids, including alkyl-imidazolium ionic liquids, and lignin derived ionic liquids.

"Aldehyde" refers to an organic compound containing the structure R—CHO, consists of a carbonyl center (a carbon double bonded to oxygen) bonded to hydrogen and an R group, which is any generic side chain.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec.butyl, tert.butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Amine" refers to an $N(R)_2$ group where the R groups can be hydrogen, alkyl, alkenyl, alkynyl, cycloalkyl, heterocycloalkyl, aryl, or heteroaryl, among others. The R groups can be the same or different. The amino groups can be primary (each R is hydrogen), secondary (one R is hydrogen) or tertiary (each R is other than hydrogen). A "tertiary amine" is an amine of the general formula $HNR_3$, where R is not H. Tertiary amines can be non-ionized or protonated to form cations. A "quaternary ammonium" is an ammonium cation of the general formula $NR_4^+$.

"Alkyl amine" refers to an alkyl group as defined within, having one or more amino groups. The amino groups can be primary, secondary or tertiary. The alkyl amine can be further substituted with a hydroxy group to form an amino-hydroxy group. Alkyl amines useful in the present invention include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group. One of skill in the art will appreciate that other alkyl amines are useful in the present invention.

"Halide" refers to a fluoride, chloride, bromide, iodide, or astatide ion or compound.

"Alkanoate" refers to an alkane acid of the form R—COO—. Alkanates of the present invention include, but are not limited to, acetate.

"Acid" refers to compounds that are capable of donating a proton ($H^+$) under the Brønsted-Lowry definition, or are electron pair acceptors under the Lewis definition. Acids useful in the present invention include Brønsted acids that include, but are not limited to, acetic acid, tartaric acid, formic acid, lactic acid, citric acid, sulfuric acid, hydrochloric acid, and nitric acid. Other organic acids and mineral acids are useful in the present invention.

"Mineral acids" are inorganic acids. Mineral acids useful in the present invention include sulfuric acid, hydrochloric acid, nitric acid, boric acid, phosphoric acid, hydrofluoric acid, hydrobromic acid, and perchloric acid.

"Hydrogen donating agent" refers to agents that are capable of participating in hydrogen transfer reactions or capable of reducing a reactant. Hydrogen donating agents useful in the present invention include tetralin, sodium formate, and formic acid. Hydrogen donating agents include those described in Pandey, 2011, and include active hydrogen donating solvents described therein.

"Base" refers to a substance that can accept protons under the Brønsted-Lowry definition, or more generally, donate a pair of valence electrons under the Lewis definition.

Bases useful in the present invention include sodium hydroxide, ammonium hydroxide, ammonia, and tertiary amines.

"Catalyst" refers to a substance that causes or accelerates a chemical reaction. Catalysts are generally not consumed in the reactions they participate in, however side reactions may inactivate, foul, or consume catalysts. Catalysts useful in the present invention include nickel, palladium, platinum, and ruthenium catalysts. Catalysts useful in the present invention also include silica-alumina catalysts.

"Oxidizing agent," "oxidant." or "oxidizer" refers to a substance that removes electrons from a reactant, removes hydrogen from a reactant, or donates an oxygen to a reactant. The oxidizing agent acts as an electron acceptor and is reduced by the electron donating reactant. Oxidizing agents useful in the present invention include $O_2$ gas, $H_2O_2$, Fenton's reagent ($H_2O_2$ in ferrous sulfate), nitrobenzene, metal oxides, and metal organic frameworks of copper or iron.

"Metal oxide" refers to the oxide of any alkaline earth metal such as Be, Mg, Ca, Sr and Ba. Other useful metals include transition metals such as Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac, as well as post transition metals such as Al, Ga, In, Tl, Ge, Sn, Pb, Sb, Bi, and Po. Exemplary metal oxides include, but are not limited to, MgO and $Al_2O_3$. One of skill in the art will appreciate that other metal oxides are useful in the present invention.

"Metal organic framework" or "MOF" as used herein refers to compounds consisting of metal ions or clusters coordinated to organic molecules to form one-, two-, or three-dimensional porous structures. MOFs are useful in catalysis and as lignin depolymerization agents. MOFs useful in the present invention include MOFs of copper and iron, such as the MOFs described in Masingale 2009.

"Lignin-derived ionic liquid" as used herein refers to any ionic liquid containing cations (e.g. tertiary amines or quaternary amines) or anions (e.g., deprotonated carboxylic acids) that are synthesized from low molecular weight lignin depolymerization products (e.g., monomer, dimer, or trimers of lignin aldehyde, alcohol, or carboxylic acid monomers).

"Reducing conditions" refers to reactions conditions that cause or accelerate the donation of electrons to a reactant. Reducing conditions useful in the present invention include reactions that contain $H_2$ gas with a suitable catalyst, polymethylhydrosiloxane, sodium cyanoborohydride, sodium borohydride, sodium borohydride-trifluoroacetic acid, and sodium triacetoxyborohydride.

"Hydride donating reducing agent" refers to reducing agents that donate a hydride to, or reduce, a reactant. Hydride donating reducing agents include $H_2$ gas with a suitable catalyst, polymethylhydrosiloxane, sodium borohydride, sodium borohydride-trifluoroacetic acid, and sodium triacetoxyborohydride.

A "salt metathesis reaction" is a chemical process involving the exchange of bonds between two reacting chemical species that results in the creation of products with similar or identical bonding affiliations. This reaction is represented by the general scheme:

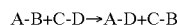

A-B+C-D→A-D+C-B

Salt metathesis is a common technique for exchanging counterions between the reacting species.

"Polar solvent" as used herein refers to solvents with a dielectric constant of about 15 or greater. Polar solvents include protic and aprotic solvents. "Protic solvents" refer to solvents that solubilize anions via hydrogen bonding and include formic acid, n-butanol, isopropanol, n-propanol, ethanol, methanol, acetic acid, nitromethane, and water. "Aprotic solvents" solvate cations via interaction with their negative dipole and include dichloromethane, tetrahydrofuran, ethyl acetate, acetone, dimethylformamide, acetonitrile, dimethyl sulfoxide, and propylene carbonate.

III. Ionic Liquids

In some embodiments, the present invention provides an ionic liquid containing at least one compound of the following formula:

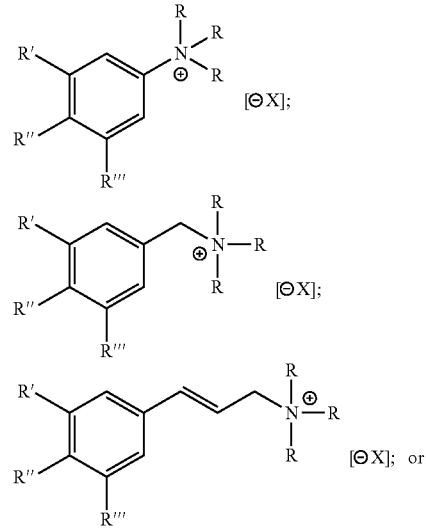

-continued

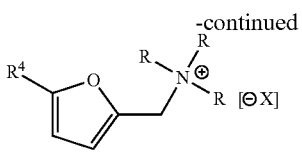

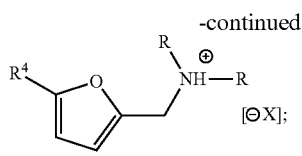

wherein each of the R groups of the nitrogen is independently selected from H, $CH_3$, or $CH_2CH_3$;
at least two of the R groups of the nitrogen are independently selected from $CH_3$, or $CH_2CH_3$;
R', R", and R'" are independently selected from H, OH, and $OCH_3$;
$R^4$ is selected from H, OH, and $CH_2OH$; and
X is an acid anion.

In some embodiments, the acid anion is acetic acid (as $CH_3CO_2^-$), formic acid (as $HCO_2^-$), lactic acid (as $CH_3CH(OH)CO_2^-$), citric acid (e.g. as $C_3H_5O(COO)_3^-$), sulfuric acid (as $HSO_4^-$), hydrochloric acid (as $Cl^-$), nitric acid (as $NO_3^-$), boric acid (as $H_2BO_3^-$), phosphoric acid (as $H_2PO_4^{-1}$), hydrofluoric acid (as $F^-$), hydrobromic acid (as $Br^-$), or perchloric acid (as $ClO_4^-$).

In some embodiments, the present invention provides a mixture containing at least two of the foregoing ionic liquids. In some embodiments, the present invention provides a mixture containing at least three of the foregoing ionic liquids. In some embodiments, the present invention provides a mixture containing at least four of the foregoing ionic liquids. In some embodiments, the present invention provides a mixture containing at least five of the foregoing ionic liquids. In some embodiments, the present invention provides a mixture containing at least six of the foregoing ionic liquids. In some embodiments, the present invention provides a mixture containing at least seven of the foregoing ionic liquids. In some embodiments, the present invention provides a mixture containing at least eight of the foregoing ionic liquids. In some embodiments, the present invention provides a mixture containing at least nine of the foregoing ionic liquids. In some embodiments, the present invention provides a mixture comprising about 10% w/v of at least one of the foregoing ionic liquids.

In some embodiments, the present invention provides tertiary ammonium ionic liquids. The tertiary ammonium ionic liquids can be produced from lignin-derived starting materials. For example, the tertiary amines can be produced from low molecular weight lignoaldehydes or lignoalcohols. Tertiary ammonium ionic liquids of the present invention include the following:

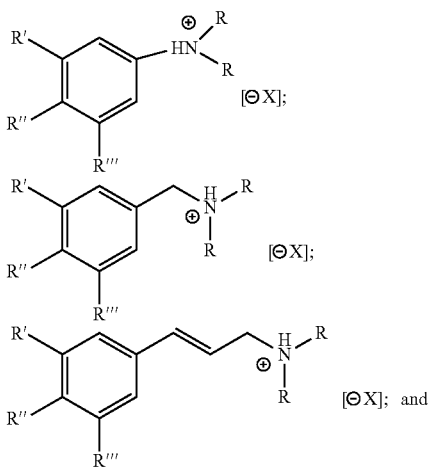

where each R group is independently selected from the group consisting of $CH_3$, and $CH_2CH_3$; R', R" and R'" are each independently selected from the group consisting of H, OH, and $OCH_3$; $R^4$ is selected from the group consisting of H, OH, and $CH_2OH$; and X represents one or more acid anions selected from the group consisting of acetic acid (as $CH_3CO_2^-$), formic acid (as $HCO_2^-$), lactic acid (as $CH_3CH(OH)CO_2^-$), citric acid (e.g. as $C_3H_5O(COO)_3^{3-}$), sulfuric acid (as $HSO_4^-$), hydrochloric acid (as $Cl^-$), nitric acid (as $NO_3^-$), boric acid (as $H_2BO_3^-$), phosphoric acid (as $H_2PO_4^-$), hydrofluoric acid (as F), hydrobromic acid (as $Br^-$), and perchloric acid (as $ClO_4^-$).

In some embodiments, the present invention provides ionic liquids prepared by
  contacting a starting material comprising lignin with a depolymerization agent to depolymerize the lignin and form a mixture of aldehyde containing compounds;
  contacting the mixture of aldehyde containing compounds with an amine under conditions suitable to convert the mixture of aldehyde containing compounds to a mixture of amine containing compounds; and
  contacting the mixture of amine containing compounds with a mineral acid under conditions suitable to form an ammonium salt, thereby preparing the ionic liquid.

In some embodiments, the invention provides ionic liquids that are contain multiple cations. For example, a compound containing one or more alcohols and one or more phenolic groups, a compound containing one or more alcohols and one or more aldehydes, a compound containing one or more phenolic groups and one or more aldehydes, a compound containing multiple aldehydes, a compound containing multiple phenolic groups, or a compound containing multiple alcohols can be aminated to form compounds with multiple tertiary amines, multiple anilines, or a combination of one or more amines and one or more analines. Such compounds may be converted to ionic liquids via salt formation as described. In some embodiments, 5-hydroxymethylfurfural can be converted to an ionic liquid containing two cationic functional groups. For example, a compound containing multiple tertiary amines can be synthesized from 5-hydroxymethylfurfural via reductive amination of the aldehyde and direct amination of the alcohol by atom-economic hydrogen autotransfer. In some cases, the corresponding tertiary ammonium can be synthesized by salt formation. In some embodiments, one or more of the multiple tertiary amines can be converted to quaternary ammonium ions via, e.g., reaction with dimethylcarbonate or dimethylsulfate.

In some embodiments, the invention provides quaternary ammonium ionic liquids. The quaternary ammonium ionic liquids can be produced from lignin-derived starting materials. For example, the quaternary ammonium ions can be produced from low molecular weight lignoaldehydes, or lignoalcohols. In some embodiments, tertiary amines are synthesized from low molecular weight lignoaldehydes, or lignoalcohols, and the quaternary ammonium ionic liquids are generated therefrom. Quaternary ammonium ionic liquids of the present invention include the following:

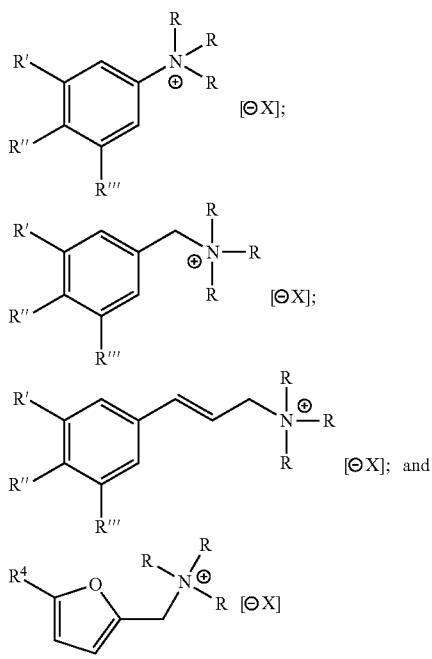

where each R group is independently selected from the group consisting of CH$_3$, and CH$_2$CH$_3$;
R', R" and R'" are each independently selected from the group consisting of H, OH, and OCH$_3$;
R$^4$ is selected from the group consisting of H, OH, and CH$_2$OH; and X represents one or more acid anions selected from the group consisting of acetic acid (as CH$_3$CO$_2^-$), formic acid (as HCO$_2^-$), lactic acid (as CH$_3$CH(OH)CO$_2^-$) citric acid (e.g. as CH$_5$O(COO)$_3^{3-}$), sulfuric acid (as HSO$_4^-$), hydrochloric acid (as Cl$^-$), nitric acid (as NO$_3^-$), boric acid (as H$_2$BO$_3^-$), phosphoric acid (as H$_2$PO$_4^-$), hydrofluoric acid (as F$^-$), hydrobromic acid (as Br$^-$), and perchloric acid (as ClO$_4^-$).

In some embodiments, the invention provides ionic liquids derived from carboxylic acid products of lignin depolymerization. Carboxylic acid derived ionic liquids of the present invention include the following:

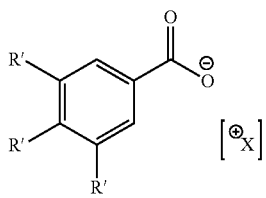

Where each R' is independently selected from the group consisting of H, OH, CH$_3$, OCH$_3$, CH$_2$CH$_3$, OCH$_2$CH3, and CH$_2$OH; and X is a cation selected from the group consisting of $^+$NR$_4$, where each R is independently selected from the group consisting of H, CH$_2$, CH$_3$, and CH$_2$CH$_3$; an imidazolium cation; a phosphonium cation; a lignin-derived tertiary ammonium cation; and a lignin-derived quaternary ammonium cation.

Figure 4:
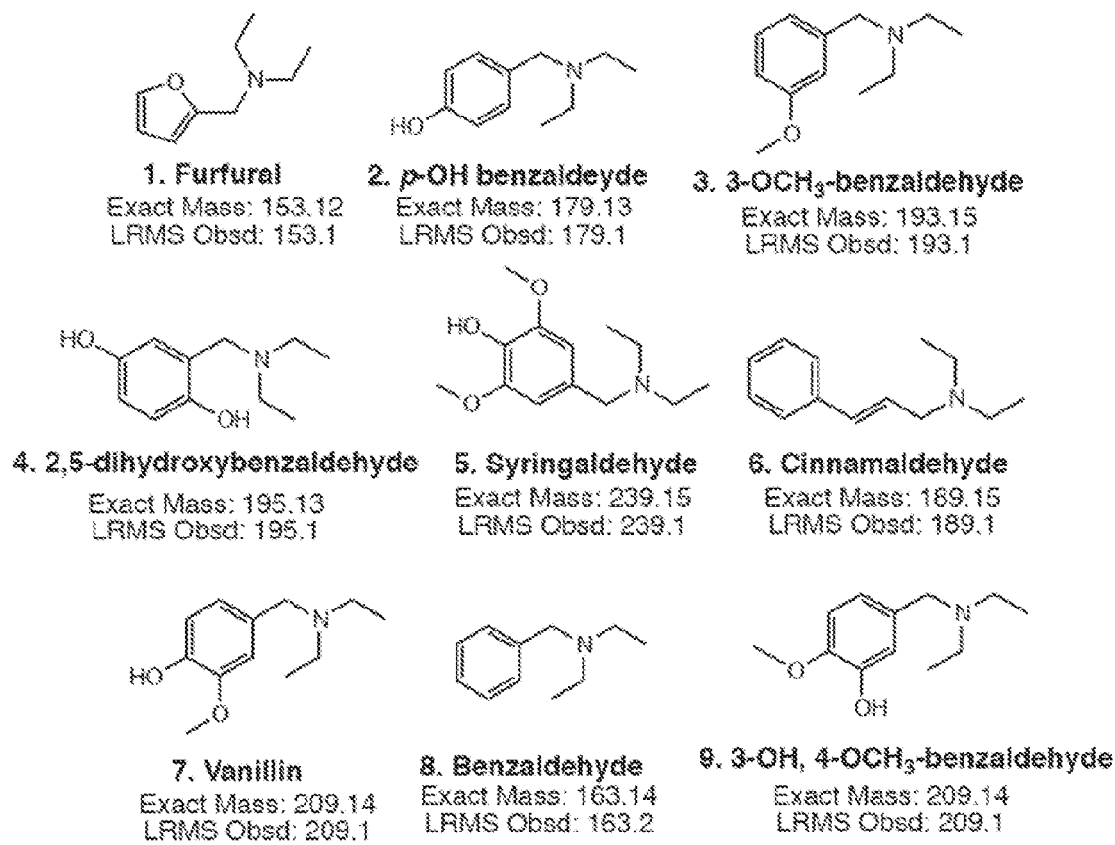
FIG. 4 depicts eight biomass-derived tertiary amines synthesized by reductive amination of diethylamine and their respective aldehydes. Compounds 2-7 and 9 are lignin-derived. Compound 1 is derived from depolymerization of hemicellulose. Compound 8 is provided as a model diethylamine. $^1$H NMR chemical shifts and gas-chromatography mass spectrometry measurements (i.e., LMRS Obsd) are provided.

In some embodiments, the ionic liquids of the present invention can be provided as mixtures. For examples, mixtures can include one or more tertiary ammonium ionic liquids, one or more quaternary ammonium ionic liquids, one or more lignoacid derived ionic liquids, or a combination thereof. In some cases, the ionic liquids of the present invention include a mixture of ionic liquids with differing anions, but the same cation. For example, an ionic liquid mixture containing a tertiary ammonium (e.g., a cation form of compound 1, 2, 3, 4, 5, 6, 7, 8, or 9 of FIG. 4, a tertiary ammonium of FIG. 7, or a cation form of the tertiary amines of FIG. 8) or a quaternary ammonium (e.g., a quaternary ammonium of FIG. 10) complexed with a mixture of different anions (e.g., anions of phosphoric or sulfuric acid). As another example, an ionic liquid mixture containing a tertiary or quaternary ammonium (e.g. NHR$_3^+$ or NR$_4^+$) complexed with a mixture of lingoacid derived anions (e.g., an anion of FIG. 9).

In other embodiments, the ionic liquids of the invention can include a mixture of ionic liquids of the same anion, but with different cations. For example, ionic liquids can include an ionic liquid mixture containing an anion of phosphoric or sulfuric acid and a mixture of cations (e.g., a mixture of one or more tertiary ammonium ions or quaternary ammonium ions). Alternatively, the ionic liquid mixtures of the invention can include a mixture containing a mixture of tertiary and/or quaternary ammonium ions (e.g., NHR$_3^+$ or NR$_4^+$) and a lignoacid derived anion (e.g., an anion of FIG. 9).

In still other embodiments, the ionic liquids of the invention can include a mixture of ionic liquids of differing anions and cations. For example, an ionic liquid mixture containing a mixture of anions (e.g., anions of phosphoric and sulfuric acid and/or lignoacid derived anions) and a mixture of tertiary and quaternary ammonium ions (e.g., two or more of a cation form of compound 1, 2, 3, 4, 5, 6, 7, 8, or 9 of FIG. 4; a tertiary ammonium of FIG. 7; a cation form of a tertiary amine of FIG. 8; or a quaternary ammonium of FIG. 10).

In some embodiments, the ionic liquids of the present invention are room temperature ionic liquids. For example, ionic liquids of the invention can be liquid at between about 4° C. and 100° C. In some cases the ionic liquids of the invention are liquid at about 10, 20, 30, 40, 50, 60, 70, 80, 90, or 100° C. In some cases, the ionic liquids have a melting point at atmospheric pressure of less than about 100° C. In some cases, the ionic liquids of the invention are liquid at one or more of the foregoing temperature under 0.1, 0.2, 0.3, 0.4, 0.5, 0.6, 0.7, 0.8, 0.9, 1, 2, 3, 4, 5, 6, 7, 8, 9, or 10 atmospheres of pressure or more. In some cases, the ionic liquid mixtures of the present invention contain a mixture of ionic liquids that are liquid at one or more of the foregoing conditions. In some cases, a room temperature solid ionic liquid of the invention is dissolved in a room temperature liquid ionic liquid of the present invention.

In some embodiments, the ionic liquids of the present invention have a high thermal stability. For example, the ionic liquids of the present invention can exhibit a high peak thermal decomposition temperature. Exemplary thermal decomposition temperatures for ionic liquids of the present invention include the thermal decomposition temperatures provided in Table 1.

TABLE 1

Thermal decomposition temperatures of selected ILs

| Ionic Liquid | Peak Decomposition Temperature (° C.) |
|---|---|
| 1a | 253 |
| 2a | 277 |
| 3a | 254 |
| 4a | 258 |

TABLE 1-continued

Thermal decomposition temperatures of selected ILs

| Ionic Liquid | Peak Decomposition Temperature (° C.) |
|---|---|
| 6a | 254 |
| 6b | 245 |
| 8a | 271 |

(a = $HSO_4^-$ ILs, b = $H_2PO_4^-$ ILs)

Figure 6:
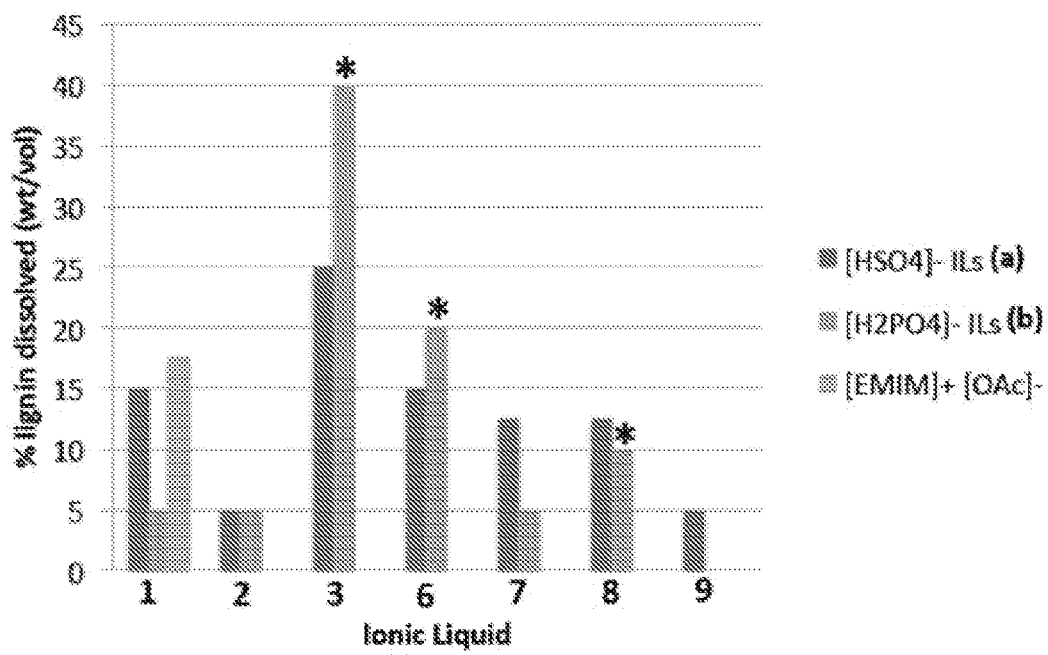
FIG. 6 depicts the dissolution properties of eighteen different lignin-derived ionic liquids consisting of nine different diethylamine cations (indicated as 1-9 across the X-axis) in complex with each of two different anions (HSO$_4$ and H$_2$PO$_4$). The ionic liquids are tested and compared to 1-ethyl-3-methyl imidazolium acetate (EMIM OAc).

In some embodiments, the ionic liquids of the present invention can dissolve lignin as shown in FIG. 6. In some embodiments, the ionic liquids of the invention can depolymerize lignin. In some cases, the ionic liquids of the present invention can dissolve and/or depolymerize lignin to a greater degree or more efficiently than other ionic liquids known in the art. Efficiency may be determined by the time or energy (e.g., heat, pressure, etc.) required for dissolving or depolymerizing the lignin. Efficiency may also be determined by the amount (e.g., weight or volume) of ionic liquid required to dissolve a given amount of lignin. Efficiency may also be determined by the maximum concentration of dissolved lignin in the one or more ionic liquids or ionic liquid mixtures of the present invention.

IV. Methods of Preparing Ionic Liquids

In some embodiments, the present invention provides methods of generating ionic liquids from the depolymerization products of lignin. In some embodiments, the present invention provides the following method:

contacting a starting material comprising lignin with a depolymerization agent to depolymerize the lignin and form a mixture of aldehyde containing compounds;

contacting the mixture of aldehyde containing compounds with an amine under conditions suitable to convert the mixture of aldehyde containing compounds to a mixture of amine containing compounds; and contacting the mixture of amine containing compounds with a mineral acid under conditions suitable to form an ammonium salt, thereby preparing the ionic liquid.

Lignin may be obtained from any method known in the art. For example, lignin may be obtained from biomass as a product of a biorefinery or a pulp or paper manufacturer. Exemplary lignins include Kraft lignin, lignosulfonate, alkali lignin, low sulfonate alkali lignin, Klason lignin, acid hydrolysis lignin, milled wood lignin (MWL), organosolv lignin, and Bjørkman lignin. Lignins may also be derived from, e.g., ionic liquid treatment of lignocellulosic biomass.

In some embodiments, the invention provides a method of extracting lignin from lignocellulosic material, where the method includes contacting the lignocellulosic material with an ionic liquid prepared by contacting a lignocellulosic material with a depolymerization agent to form a mixture of aldehyde containing compounds, contacting the mixture of aldehyde containing compounds with an amine under suitable conditions to convert the aldehyde containing compounds to a mixture of amine containing compounds and contacting the mixture of amine containing compounds with an acid under conditions suitable to form an ammonium salt, under conditions suitable to extract the lignin. In some cases, the method of extracting the lignin depolymerizes the lignin.

Methods for obtaining lignin from lignocellulosic biomass can be broadly grouped into two categories. The first group includes methods in which the cellulose and hemicellulose are removed by solubilization, leaving lignin as an insoluble residue. The second group includes methods involving dissolution and removal of lignin, leaving cellulose and hemicellulose as insoluble residues, followed by recovery of lignin from solution.

Alternatively, the lignin starting material may be provided as lignocellulosic biomass. The lignin or lignocellulosic biomass may be pretreated by methods known in the art prior to, or simultaneously with, lignin extraction or depolymerization. Pre-treatment methods include mechanical grinding, chipping, cracking, fracturing, sawing, heating, boiling, steam explosion, ammonia fiber expansion, microwave or ultrasound irradiation, contacting with a dilute acid, a base, a concentrated acid, $CO_2$, hot water, an organic solvent, an ionic liquid, hot water, or a combination of physical and/or chemical pre-treatment steps.

Pretreatment conditions can also include use of ionic liquids (e.g. ionic liquids known in the art or ionic liquids of the present invention) and dilute acid. For example, 1, 2, 3, 4, 5, 6, 7, 8, 9, 10, 11, 12, 13, 14, 15, 16, 17, 18, 19, or about 20% hydrochloric acid and an ionic liquid can be used to pretreat biomass and simultaneously depolymerize cellulose to monomeric sugars.

Pretreatment conditions can also include the use of a co-solvent. Co-solvents can include water, an organic solvent, or an additional ionic liquid. In some cases, co-solvent can be used to lower the volume or concentration requirement of the ionic liquid. In some embodiments, the ionic liquids of the present invention are useful as co-solvents or in combination with co-solvents for treatment of lignocellulosic biomass.

A. Depolymerization

Figure 2:
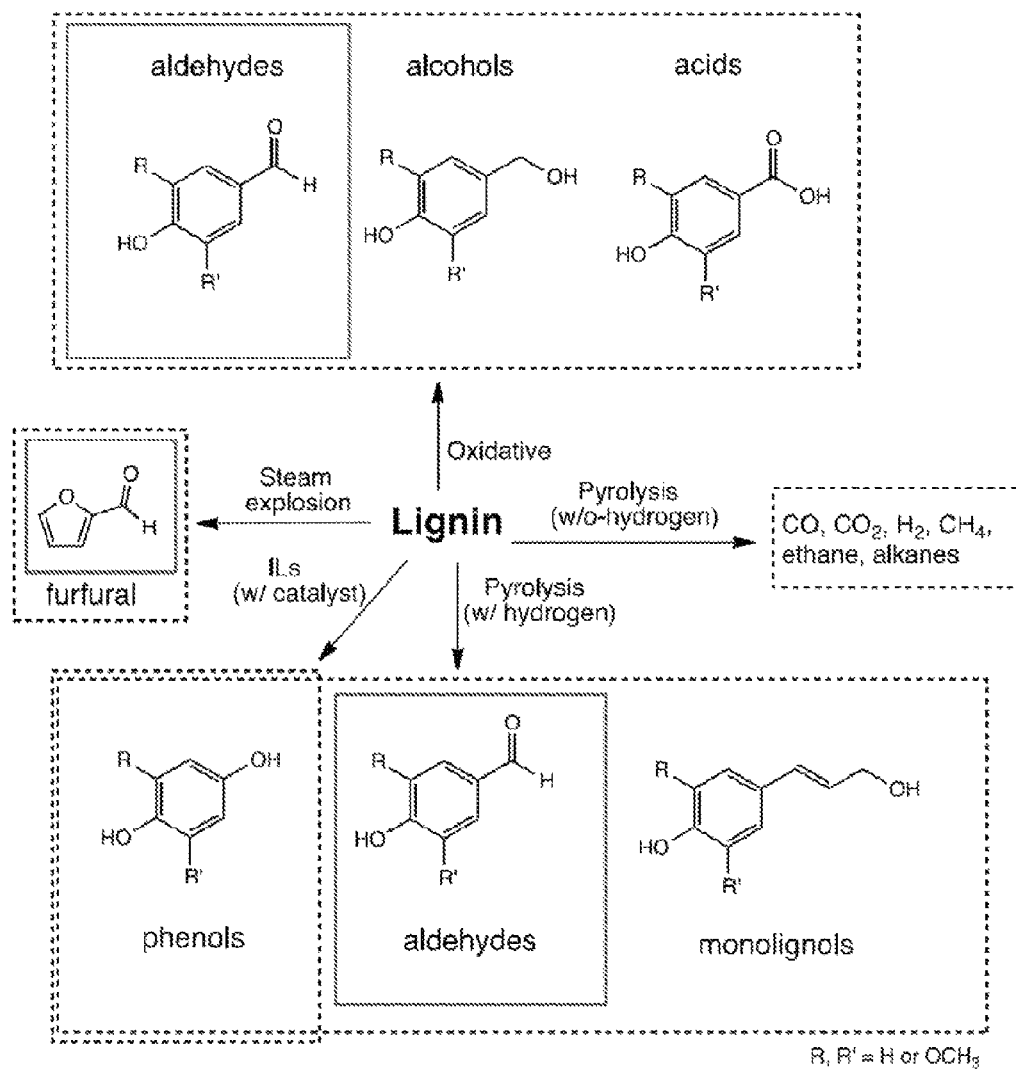
FIG. 2 depicts products of various methods for depolymerization of lignins. Dashed boxes represent major products from an indicated method. Aldehydes, alcohols, and carboxylic acids are produced in a variety of traditional (e.g., oxidative, pyrolysis, steam explosion) and emerging (e.g., ionic liquid) methods.

The present invention provides methods for contacting the lignin with a depolymerization agent. Depolymerization agents include any chemical or process known in the art for depolymerizing polymeric lignin to low molecular weight compounds (e.g., monomers, dimers, trimers, etc.). In some cases, the depolymerizing agent extracts and depolymerizes the lignin from a lignocellulosic biomass. In other cases, the lignin must be extracted prior to the step of contacting the lignin with a depolymerizing agent. Processes and agents suitable for depolymerizing lignin include those described in, e.g. Pandey, (2011); Pearl, (1942); Liu, (2013); Kleen, (1991); and Xiang, (2000). Exemplary embodiments of lignin depolymerization methods and examples of low molecular weight compounds thus produced are depicted in FIG. 2, and include oxidative methods which provide aldehydes, alcohols, and acids; steam explosion which provides the hemicellulose depolymerization and dehydration product furfural or 5-hydroxymethylfurfural; contacting with ionic liquids and a catalyst which provides phenols; and oxidative methods or pyrolysis with hydrogen which provide aldehydes, alcohols, and carboxylic acids.

Depolymerization agents include one or more of ionic liquids or ionic liquid mixtures (including the ionic liquids or ionic liquid mixtures of the invention), hydrogenolysis (e.g., $H_2$ gas, a hydrogen donating agent such as tetralin, sodium formate or formic acid), a dilute acid, a concentrated acid, a base, an oxidizing agent (e.g., nitrobenzene, a metal oxide, hydrogen peroxide, or $O_2$ gas with an appropriate catalyst). Fenton's reagent ($H_2O_2$ and ferrous sulfate), metal organic frameworks of copper or iron, and ammonium hydroxide.

Depolymerization agents can include methods and conditions that provide a high yield of aromatics or a higher yield of aromatics as compared to non-aromatic low molecular weight compounds. Depolymerization agents can also include methods and conditions that provide one or more of low molecular weight aldehydes, alcohols, or carboxylic acids. In some cases, depolymerization agents can include methods and conditions that provide one or more of low molecular weight aromatic aldehydes, alcohols, or carboxylic acids. In other cases, depolymerization agents can include methods and conditions that provide a high yield (e.g., 5%, 10%, 15%, 20%, 25%, 30%, 35%, 40%, 45%, 50%, 55%, 60%, 65%, 70%, 75%, 80%, 85%, 90%, 95%, 99% or more) of aromatic aldehydes, alcohols, or carboxylic acids. In some embodiments, depolymerization agents can include methods and conditions that efficiently convert lignin, e.g. convert 35%, 40%, 50%, 55%, 60%, 65%, 70%, 75%, 80%, 85%, 90%, 95%, 99%, or 100% of the lignin in the starting material (e.g., lignin or lignocellulosic biomass) into low molecular weight compounds.

Depolymerization agents of the present invention can include methods and conditions that predominantly yield low molecular weight aldehydes or low molecular weight aromatic aldehydes. In some cases, depolymerization agents can include methods and conditions that provide, or generally provide, a high yield of aldehydes or aromatic aldehydes. Additionally, depolymerization agents can include methods and conditions that provide more aldehydes than carboxylic acids or more aldehydes than alcohols.

Depolymerization agents include the methods and conditions provided in Pearl, (1942). For example, lignin or lignocellulosic biomass may be contacted with $CuSO_4$ and NaOH under conditions that yield aldehydes. In some cases, depolymerization agents, such as $CuSO_4$ and NaOH can be utilized to yield particular aldehydes including vanillin and syringaldehyde. Depolymerization agents also include the methods and conditions provided in Liu, (2013). For example, lignin or lignocellulosic biomass may be contacted with quaternary ammonium and imidazolium dimethylphosphate ionic liquids. Such conditions are known to efficiently depolymerize lignin and provide aldehydes such as vanillin, p-hydroxybenzaldehyde, and syringaldehyde in moderate yields.

Depolymerization agents of the present invention can include methods and conditions provided in Villar, (2001). For example, lignin or lignocellulosic biomass may be contacted with mild oxidants such as nitrobenzene, metal oxides, and oxygen to produce aldehydes. Similarly, depolymerization with metal organic frameworks of $Cu^{2+}$, $Fe^{3+}$, or combinations of metal ions can be used as oxidants for lignin depolymerization. Alternatively, hydrogen peroxide or Fenton's reagent may be utilized for oxidative lignin depolymerization. As yet another embodiment, oxidation may be performed under alkaline conditions.

Depolymerization agents of the present invention can include methods and conditions that predominantly yield low molecular weight alcohols or low molecular weight aromatic alcohols. In some cases, depolymerization agents can include methods and conditions that provide, or generally provide, a high yield of alcohols or aromatic alcohols. Additionally, depolymerization agents can include methods and conditions that provide more alcohols than carboxylic acids or more alcohols than aldehydes. In some cases, depolymerization can include methods that provide phenols, a high yield of phenols, phenols as a predominant product, or a greater proportion of phenols as compared to carboxylic acids or aldehydes.

Depolymerization agents include the methods and conditions provided in Kleen, (1991). For example lignocellulosic biomass may be subject to fast pyrolysis. In some cases, fast pyrolysis depolymerization can provide alcohols such as 4-Methyl guaiacol, 4-vinyl guaiacol, trans-isoeugenol, trans-coniferyl alcohol, and aldehydes such as vanillin, and coniferaldehyde as the predominant products of lignin depolymerization. In some cases, fast pyrolysis can result in alcohols such as guaiacol, 4-vinyl guaiacol, and trans-isoeugenol as the predominant products of lignin depolymerization. In still other cases, pyrolysis can provide guaiacol, syringol, and 4-vinyl syringol as the predominant products of lignin depolymerization.

Depolymerization agents include the methods and conditions for hydrogenolysis. In some cases, hydrogenolysis can provide phenols. In some cases, hydrogenolysis is performed at about 300-600° C. in the presence of an active hydrogen donator such as a solvent or hydrogen gas. Suitable hydrogen donating solvents include tetralin, sodium formate, or formic acid.

Depolymerization conditions also include base catalyzed depolymerization, such as described in U.S. Pat. No. 5,959,167. For example, the lignin can be contacted with a base (e.g., an alkali hydroxide) in the presence of a supercritical alcohol (e.g., methanol, ethanol, etc.). In some cases, the base catalyzed depolymerization can provide a mixture of depolymerized lignin products including alkylated phenols (e.g., mono, di, tri, and polysubstituted phenols and alkylated benzenes), alkylated benzenes, and alkoxybenzenes.

Depolymerization can be performed at any suitable temperature, pressure, or pH. Suitable temperatures, pressures, and pH for depolymerization can be determined by those of skill in the art. In some cases, the ionic liquids of the present invention provide for pre-treatment or lignin depolymerization at a reduced temperature or pressure.

In some embodiments, the depolymerization products can be directly converted by subsequent methods of the present invention into amines or acids suitable for ionic liquid cations or anions respectively without extensive purification. For example, lignin may be depolymerized and amination or deprotonation may be performed on the depolymerization products without purifying, or substantially purifying, the depolymerization products from other components of lignocellulosic biomass. In some cases, the lignin may be depolymerized and amination or deprotonation may be performed on the depolymerization products without purifying, or substantially purifying, individual depolymerization products or individual classes of depolymerization products (e.g., aldehydes, alcohols, phenols, carboxylic acids).

In some cases, the predominant products of the depolymerization process may be determined and used to guide the choice of subsequent amination or deprotonation steps. For example, if aldehyde depolymerization products predominate, then reductive amination may be chosen as a suitable amination step. Alternatively, if alcohol depolymerization products predominate, then atom-economic hydrogen autotransfer may be utilized to form tertiary amines from the alcohols. As another example, if phenol alcohols predominate, then tertiary amines may be obtained via conversion of the phenols to aniline as provided herein. As yet another example, if carboxylic acids are present in the mixture of depolymerization products as a predominate constituent, then anions may be obtained via deprotonation. Alternatively, the choice of amination or deprotonation may be determined regardless or in spite of the predominant depolymerization product.

Alternatively, lignin may be depolymerized and the depolymerization products can be purified. Methods and compositions are known in the art for purifying lignin depolymerization products. In some cases, a purification method may be chosen that yields one or more of lignin derived alcohols, aldehydes, or carboxylic acids.

In some embodiments, the step of contacting the starting material with a depolymerization agent includes contacting the starting material with one or more of the following compositions: an ionic liquid such as an imidazolium ionic liquid or a lignin-derived ionic liquid; a hydrogen gas; a hydrogen gas and a catalyst; a hydrogen donating solvent such as tetralin, sodium formate, and formic acid; a dilute acid; a concentrated acid; a base; a catalyst and an oxidizing agent such as nitrobenzene, metal oxide, hydrogen peroxide, or oxygen gas; Fenton's reagent; a metal organic framework of copper or iron; or ammonium hydroxide. In some embodiments, the depolymerization agent is a lignin derived ionic liquid. In some embodiments, the depolymerization agent is an imidazolium ionic liquid.

Aldehyde lignin depolymerization products include:

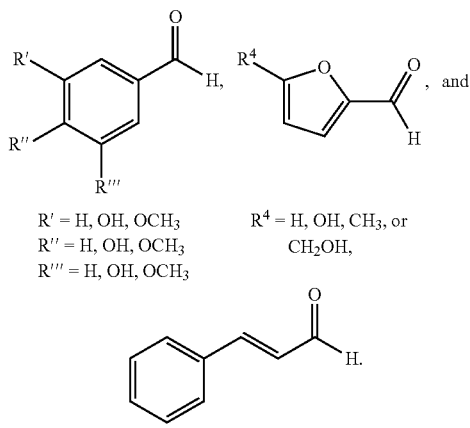

R' = H, OH, OCH₃
R'' = H, OH, OCH₃
R''' = H, OH, OCH₃

R⁴ = H, OH, CH₃, or CH₂OH,

Alcohol lignin depolymerization products include p-coumaryl alcohol, coniferyl alcohol, sinapyl alcohol,

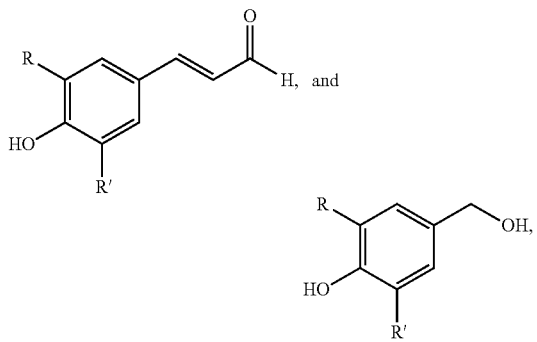

wherein R and R' are selected from the group consisting of H and OCH₃.

Alcohol lignin depolymerization products also include the following phenols:

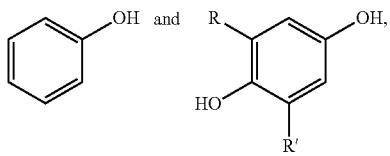

wherein R and R' is independently selected from the group consisting of H and OCH₃.

Lignoacid depolymerization products of the present invention include the following carboxylic acids:

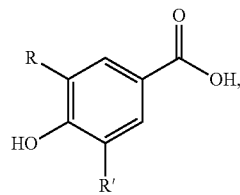

where R and R' are each selected from the group consisting of H, CH3, OH, and OCH₃.

In some cases lignin depolymerization products, e.g., vanillin, syringaldehyde, a lignin derived aldehyde, or a derivative thereof, can be converted to a methoxy, dimethoxy or trimethoxy derivative. For example, vanillin can be converted into 3.4dimethoxybenzaldehyde. As another example, syringaldehyde can be converted into 3,4,5 trimethoxybenzaldehyde. The conversion can be performed using methods known in the art. For example, vanillin, syringaldehyde, and/or another lignin derived aldehyde can be dissolved in aqueous alkaline hydroxide (e.g., NaOH), to which an alkylating agent such as dimethylsulfate is added under reflux conditions for at least about 30 minutes-1 h or more. In some cases, the desired methoxy derivative is obtained as a phase separated oil.

B. Amination and Deprotonation

Figure 5:
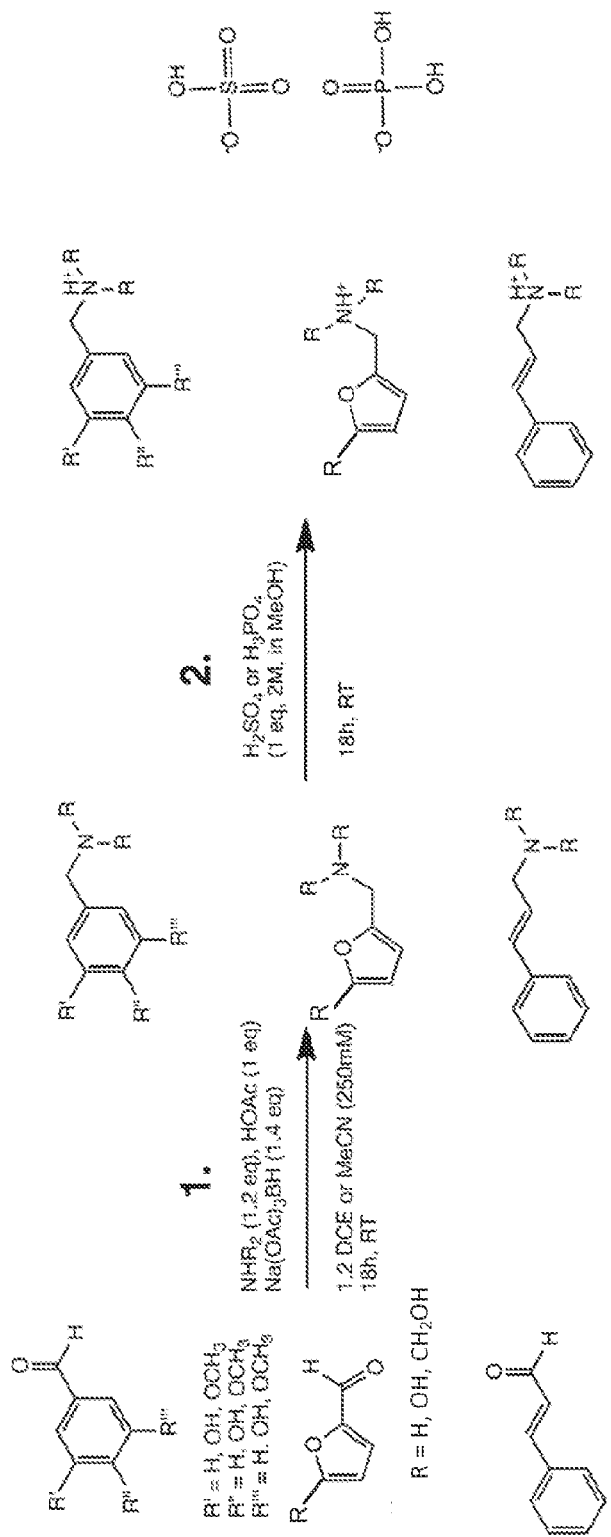
FIG. 5 depicts a reaction scheme for generating ionic liquids from monolignoaldehydes.

Lignin depolymerization products (e.g., mono, di, tri, etc. lignoaldehydes, their methoxy derivatives, or lignoalcohols) can be aminated to form amines or ammonium ions, e.g. tertiary amines or quaternary ammonium ions. In some embodiments, tertiary amines can be formed from lignoaldehydes via an amination step, e.g. as shown in FIG. 5. For example, furfural, 5-hydroxymethylfurfural, p-hydroxybenzaldehyde, 3-methoxybenzaldehyde, 2,5-dihydroxybenzaldehyde, syringaldehyde, cinnamaldehyde, vanillin, benzaldehyde, or 3-hydroxy,4-methoxybenzaldehyde may be treated with a secondary amine to produce a tertiary amine. In some cases, the tertiary amines or quaternary ammonium ions thus synthesized can be purified. In other cases, they can be utilized in the reaction vessel without significant purification for downstream processes, e.g., biomass treatment or synthesis of ionic liquids.

Suitable secondary amines (HNR₂) can be used to provide various tertiary amines depending on the amino-R group chosen. For example, an aldehyde lignin depolymerization product may be treated with a dialkylamine to produce a dialkyl tertiary amine. Suitable dialkylamines include cyclic and acyclic dialkylamines. In some cases, the two R groups of the dialkylamine are the same (e.g., diethylamine). In other cases, the two R groups of the dialkylamine are different (e.g., N-ethylmethylamine). In some cases, a mixture of secondary amines may be utilized to provide a mixture of lignin-derived tertiary amines.

In some cases, lignin-derived secondary amines, or mixtures thereof, can be synthesized by amination of low molecular weight lignin depolymerization with one or more primary amines. Suitable primary amines include ammonia, ethylamine, methylamine, an alkylamine, a cycloalkylamine, or an acyclic alkylamine.

a. Reductive Amination

In some embodiments, the step of contacting the mixture of aldehyde containing compounds with an amine is performed under reducing conditions. For example, aldehydes may be aminated with a secondary amine to form tertiary amines via reductive amination. Conditions and methods for reductive amination are known in the art. For example, reductive amination may be performed according the conditions of FIG. 5.

In some embodiments, the reducing conditions include an amine, and an acid such as a Brønsted acid. In some embodiments, the reducing conditions include an amine, a Brønsted acid, and a hydride reducing agent. Suitable Brønsted acids include aromatic and aliphatic carboxylic acids. In some embodiments, the Brønsted acid is formic acid, acetic acid, proprionic acid, or an aromatic carboxylic acid. In some embodiments, the, the Brønsted acid is acetic acid. In some embodiments, the reducing conditions include about 1-2 equivalents of, the Brønsted acid. Reductive amination may also be carried out with other suitable acids as known in the art.

In some embodiments, the reducing conditions comprise about 1-2 equivalents of the amine. In some embodiments, the amine is a cyclic amine, acyclic amine, monoamine, or dialkylamine. In one embodiment, the amine is a dialkylamine. In some cases, the amine is diethylamine.

Reductive amination can be performed with a suitable reducing agent. In some embodiments, the reducing agent is sodium triacetoxyborohydride, sodium cyanoborohydride, sodium borohydride-trifluoroacetic acid, hydrogen gas with an appropriate catalyst, or polymethylhydrosilane. In some cases, the reducing agent is a silane reducing reagent, a borane with diacid such as BF3.THF with phthalic acid or succinic acid, or a reducing agent described in Lu, 2002. In some embodiments, the reducing agent is sodium triacetoxyborohydride.

Amines, acids and reducing agents may each be included in the reductive amination reaction at a ration with respect to the aldehyde of about 1-1, 1-1.1, 1-1.2, 1-1.3, 1-1.4, 1-1.5, 1-1.6, 1-1.7, 1-1.8, 1-1.9, 1-2, 1-3, 1-4, or about 1 mole of aldehyde for every 5 moles of amine, acid, or reducing agent. In some embodiments, the reducing conditions include about 1-2 equivalents of the reducing agent.

Reductive amination can be performed in a suitable solvent or solvent system. In general, a solvent or solvent system is chosen that dissolves the aldehyde and amine reactants and, optionally the reducing agent as well. In some cases, a solvent or solvent system is chosen that dissolves the reactants, but not the product. Such solvents or solvent systems allow facile purification of the products. In other cases, a solvent or solvent system is chosen that solubilizes the products. In some cases, a solvent or solvent system is chosen that is compatible with upstream and/or downstream processes. For example, a solvent or solvent system that is compatible with biomass treatment or pretreatment, lignin extraction, or lignin depolymerization may be utilized in the methods of the present invention for reductive amination.

Suitable solvents for reductive amination of aldehydes include 1,2-dichloroethane, dichloromethane, THF, methanol, ethanol, isopropanol, acetic acid, NMP, toluene, dimethylacetamide, DMF, ether, or acetonitrile. Other suitable solvents include solvents described in Abdel-Magid, 2006.

Tertiary amines generated by the reductive amination methods of the present invention include the following compounds

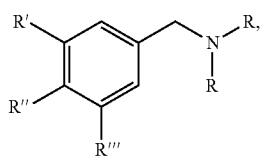

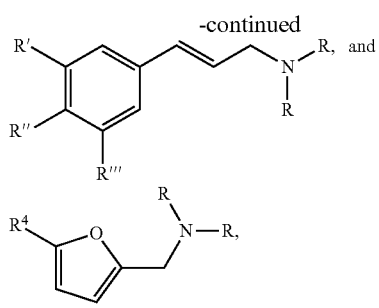

where each R is independently selected from the group consisting of $CH_3$, and $CH_2CH_3$; R', R", and R''' are each independently selected from the group consisting of H. OH, and $OCH_3$; and $R^4$ is selected from the group consisting of H. OH, and $CH_2OH$. The tertiary amines of the present invention also include compounds 1, 2, 3, 4, 5, 6, 7, 8, or 9 of FIG. 4, or mixtures thereof.

b. Direct Amination

Figure 7:
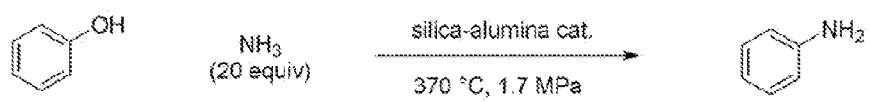
FIG. 7 depicts a reaction scheme for generating ionic liquids from monolignol phenol alcohols. (A) Phenols can be directly aminated via processes known in the art using various amines (e.g., ammonia, dialkyl amine, R$_2$NH, etc.). See, Kahl (2005). (B) Products of the amination reaction can be converted to ionic liquids via, e.g., salt formation.
Figure 7:
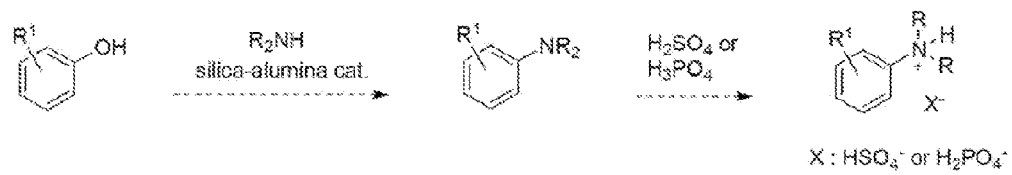
Figure 8:
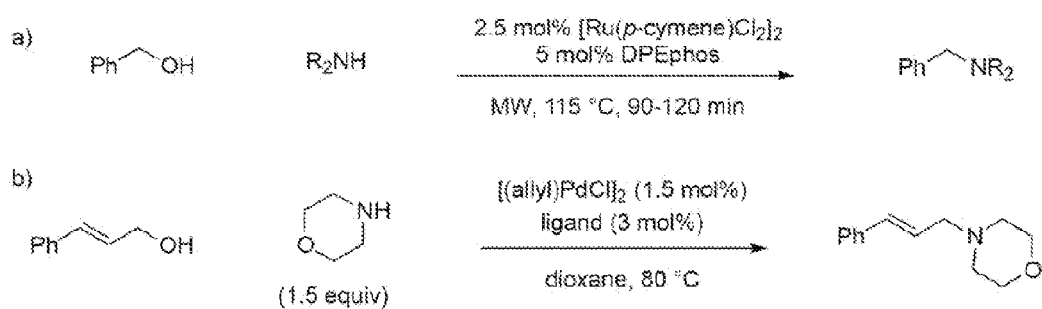
FIG. 8 depicts a reaction scheme for generating amines from (A) benzylic and (B) allylic monolignol alcohols via atom-economic hydrogen autotransfer. The amines, thus generated, can be converted to ionic liquids via, e.g., salt metathesis. Lignin depolymerization via acid hydrolysis or ionic liquid treatment, for example, can provide a ready source of these alcohols.

The methods of the present invention also provide for direct amination. For example, direct amination of lignin depolymerization products can be utilized to provide tertiary amines. In some cases, phenols or other lignoalcohols can be directly aminated. Direct amination includes atom economic hydrogen autotransfer of benzylic and allylic alcohols (FIG. 8) as well as the generation of anilines from phenol alcohols (FIG. 7). Exemplary methods of direct amination of phenols to anilines include the methods described in Kahl, (2005).

Direct amination of phenols can be performed using a variety of suitable catalysts. For example, direct amination of phenols can be performed with a silica-alumina catalyst, $TiO_2$—$SiO_2$, palladium on alumina with metal oxides (e.g., BaO), gallium containing zeolites, NaOH, $(C_2H_3O)_2POCl$ then potassium metal and $KNH_2$. in liquid ammonia, and the catalysts described in Rossi, 1972. Suitable silica-alumina catalysts of the present invention include the catalysts described in U.S. Pat. No. 4,987,260.

In some embodiments, direct amination of unsubstituted phenols derived from lignin depolymerization can be performed by nitration with, e.g., sulfuric acid and sodium nitrate. In some cases, the product can then be reduced with, e.g., sodium borohydride or other suitable reducing agent.

Direct amination of phenols can be performed with a variety of suitable amines. As provided above, direct amination of phenols can be performed with amines of the general formula $HNR_2$. For example, suitable secondary amines can be used to generate anilines of the following structure:

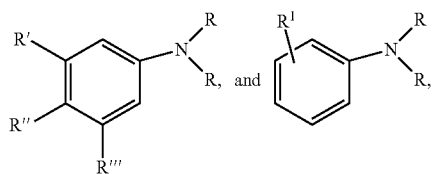

where each R is independently selected from the group consisting of $CH_2$, and $CH_2CH_3$; and R', R", R''', and $R^1$ are independently selected from the group consisting of H, OH, $OCH_3$, $OCH_2CH_3$, $CH_3$, and $CH_2CH_3$.

Direct amination of phenols may be performed at elevated temperatures and pressures. For example, direct amination of phenols can be performed at between about 200° C. to about 500° C., between about 250° C. to about 450° C., between about 300° C. to about 400° C., or at about 350° C., 360° C., 370° C., 380° C., 390° C., or 400° C. In some embodiments, direct amination of phenols can be performed at about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.2, 2.5, or about 3 MPa.

The anilines synthesized by direct amination of phenols may be protonated by a variety of methods known in the art to form ionic liquids. For example, FIG. 7b describes protonation with a mineral acid such as sulfuric or phosphoric acid. In some cases, mixtures of ionic liquids are formed by protonation of an aniline with a mixture of acids. In other cases, mixtures of ionic liquids are synthesized by protonation of a mixture of anilines with an acid or a mixture of acids.

Direct amination of benzylic and allylic lignin-derived alcohols can be performed via atom-economic hydrogen autotransfer as described herein. Direct amination of benzylic alcohols via atom-economic hydrogen autotransfer can be performed according to the scheme outlined in FIG. 8a. For example benzylic alcohols can be aminated with a suitable secondary amine of the general formula $HNR_2$ in the presence of a ruthenium catalyst at high temperature in a suitable solvent. In some cases, the reaction involves oxidation of the alcohol to a carbonyl compound with a transition metal catalyst, imine formation between the carbonyl compound and an amine, and reduction of the imine with a transition metal catalyst. Suitable transition metal catalysts include ruthenium, nickel, rhodium, iridium catalysts such as $[Cp*IrCl]_2$, and ruthenium based catalysts such as $[Ru(p-cymene)Cl_2]_2$. Suitable solvents include the alcohol being aminated, and Bis-[2-(diphenylphosphino)phenyl] ether. In some cases, the reaction can be performed in the absence of solvent. In some cases, the reaction can be performed under microwave irradiation. The catalyst can be used at about 1, 1.5, 2, 2.5, 3, or about 4 mol %. The solvent can be used at about 1, 2, 3, 4, 5, 6, 7, 8, 9, 10, 11, 12, 13, 14, 15 mol %. Suitable temperatures include about 25° C. to about 200° C., about 35° C. to about 190° C., 45° C. to about 180° C., 55° C. to about 170° C., 65° C. to about 160° C., 75° C. to about 150° C., 85° C. to about 140° C., 95° C. to about 130° C., 105° C. to about 120° C., or about 115° C.

Direct amination of allylic alcohols can be performed by a variety of suitable methods including the scheme outlined in FIG. 8b. A variety of secondary amines can be utilized in the amination step including morpholine and derivatives thereof. The amination can be catalyzed by a palladium catalyst such as $[PdCl]_2$ at about 0.5, 0.75, 1, 1.5, or about 2 mol %, and a ligand such as a bidentate phosphine ligand at about 0.5, 0.75, 1, 1.5, 2, 3, 3.5, 4, 5.5, or about 6 mol %. The reaction can be performed in a variety of suitable solvents as known in the art including dioxane. The amination can be performed at about 25° C. to about 150° C., about 35° C. to about 145° C., 45° C. to about 140° C., 55° C. to about 135° C., 65° C. to about 130° C., 75° C. to about 125° C., 85° C. to about 120° C., or about 70, 75, 80, 85, or 90° C. Suitable transition metal catalysts include ruthenium based catalysts such as $[Ru(p-cymene)C_2]_2$, nickel, rhodium, and iridium based catalysts such as $[Cp*IrCl]_2$. Suitable solvents include dioxane, DMF, acetonitrile, toluene, the alcohol being aminated, and Bis-[2-(diphenylphosphino)phenyl]ether. In some cases, the reaction can be performed in the absence of solvent. In some cases, the reaction can be performed under microwave irradiation.

In some embodiments, direct amination of allylic and benzylic alcohols provides compounds of the following structures:

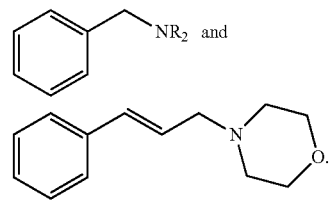

c. Deprotonation

Figure 9:
FIG. 9 depicts a reaction scheme for generating ionic liquids from lignin-derived carboxylic acids.
Figure 10:
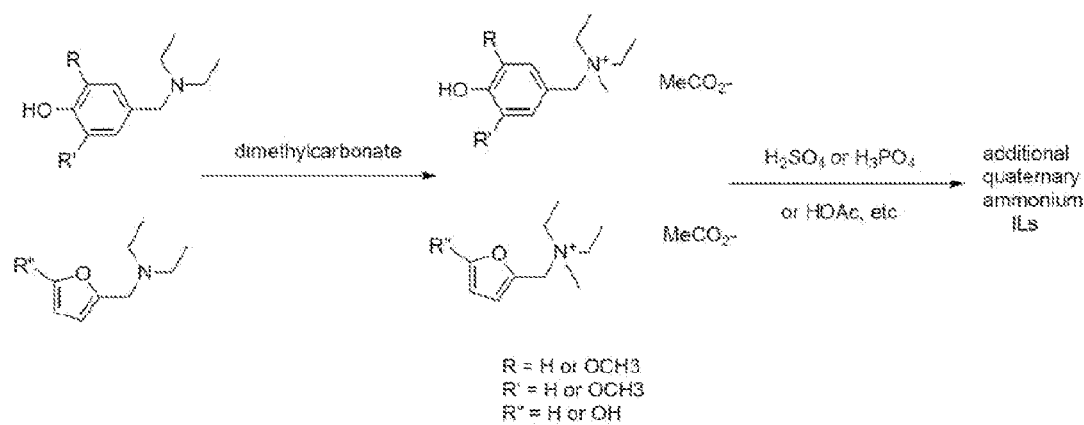
FIG. 10 depicts a reaction scheme for generating quaternary ammonium ions from tertiary amines.

Lignoacids, such as lignin-derived carboxylic acids, including aromatic carboxylic acids can be deprotonated by the methods of the present invention to provide anions suitable for use in an ionic liquid as depicted in FIG. 9. For example, the carboxylic acids can be deprotonated with bicarbonate in the presence of a quaternary ammonium ion. Suitable quaternary ammonium ions include quaternary ammonium ions of the general formula $R_4N^+$, wherein each R is independently selected from H, $CH_3$, $CH_2CH_3$, an alkyl, a cyclic alkyl, and an acyclic alkyl.

In some embodiments, deprotonation of lignin derived carboxylic acids can provide ionic liquids of the following structure:

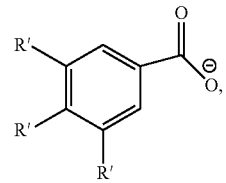

wherein each R' is independently selected from the group consisting of H, OH, $OCH_3$, $OCH_2CH_3$, $CH_3$, and $CH_2CH_3$, including but not limited to:

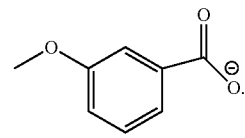

C. Alkylation of Tertiary Amines

In some embodiments, the present invention provides for generating quaternary amines from tertiary amines such as the tertiary amines provided above. For example, quaternary amines may be generated via the methods and compositions described in Aresta, (2002), Adelworer, (2002), Fabris, (2009), Smiglak, (2010), Chiappe, (2011), or Holbrey, (2002), or a combination thereof. In some cases, dimethylsulfate or dimethyl carbonate or another methylating agent or alkylating agent (e.g., methyl halide or alkyl halide) may be utilized to generate quaternary amines from tertiary amines of the present invention. In some cases, the synthesis of quaternary amines from tertiary amines can be performed according to the scheme outlined in FIG. 10. Ionic liquids can be obtained from the resulting quaternary amines via contact with an acid such as a mineral acid or a Brønsted acid such as acetic acid. Alkylation of lignin derived tertiary amines of the present invention can provide the following structures:

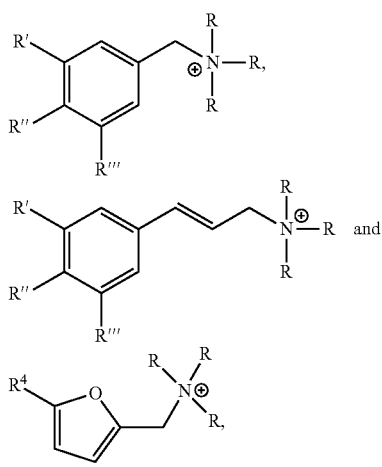

where each R is independently selected from the group consisting of $CH_3$, and $CH_2CH_3$, each R', R", and R''' are independently selected from the group consisting of H, OH, and $OCH_3$; and $R^4$ is selected from the group consisting of H, OH, $CH_3$, and $CH_2OH$.

D. Salt Formation

In some embodiments, the methods of the present invention provide for ionic liquid synthesis from tertiary amines via a salt formation reaction. In some cases, the step of contacting the mixture of amine containing compounds with an acid under conditions suitable to form an amine salt is a salt metathesis reaction. In some cases, ionic liquids of the present invention can be synthesized from lignin derived tertiary amines, including the tertiary amines provided herein, by a salt formation reaction. In some cases, the present invention provides methods and compositions for ionic liquid synthesis from the tertiary amines of one or more of compounds 1, 2, 3, 4, 5, 6, 7, 8, or 9 of FIG. 4. A scheme for synthesis of ionic liquids from tertiary amines of the present invention is described in FIG. 5 step 2.

In some cases, the ionic liquids are formed as a mixture. For example ionic liquids can be synthesized from two or more (e.g., 2, 3, 4, 5, 7, 8, 9, 10, 11, 12, 13, 14, 15, 16, 17, 18, 19, 20 or more) tertiary amines of the present invention in a single reaction vessel. As another example, the mixture can be synthesized by utilizing more than one acid, such as acetic acid or more than one mineral acid (e.g., hydrochloric, nitric, phosphoric, sulfuric, boric, hydrofluoric, hydrobromic, or perchloric acid). In some cases, a mixture of ionic liquids can be synthesized via salt formation between two or more tertiary amines and two or more acids (e.g. two or more mineral acids and/or acetic acid) in a single reaction vessel. As such, mixtures of ionic liquids can be synthesized in a single reaction vessel that contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more ionic liquids. In some cases, such mixtures can contain between about 2 and about 200 different ionic liquids. In some embodiments, the steps of contacting the starting material, contacting the mixture of aldehydes with an amine, and contacting the mixture of amine containing compounds are performed in a single reaction vessel.

Salt formation reactions of the present invention can include a polar solvent. In some embodiments, the conditions of the salt formation reaction include acid in a polar solvent. In some embodiments, the conditions of the salt metathesis reaction include acid in a polar solvent. Suitable polar solvents are known in the art and include, e.g., water, dioxane, acetonitrile, nitromethane, ethylene glycol, and an alcohol such as methanol, ethanol, propanol, etc. In some embodiments, the polar solvent is methanol.

Salt metathesis reactions of the present invention can include an acid, such as a mineral acid (e.g., hydrochloric, nitric, phosphoric, sulfuric, boric, hydrofluoric, hydrobromic, or perchloric acid). In some embodiments, the acid is a mineral acid such as sulfuric or phosphoric acid. The acid can be at about 0.5 M, 0.6 M, 0.7 M, 0.8 M, 0.9 M, 1 M, 2 M, 3 M, or about 4 M. In some cases, the acid is provide at about 0.5, 0.6, 0.7, 0.8, 0.9, 1.0, 1.1, 1.2, 1.3, 1.4, 1.5, 1.6, 1.7, 1.9, 2, 3, 4, or about 5 equivalents of the amine. The reaction can be carried out at a temperature of about 10, 12, 15, 17, 18, 20, 22, 24, 25, 27, 30, 35, 37, 40, 42, 45, 50, 55, 60, or about 65° C. The salt metathesis can be performed for about 1, 2, 3, 4, 5, 7, 10, 12, 14, 15, 16, 17, 18, 19, 20, 22, 24, 28, 30, 34, 36, 38, 40, 45, 48, or about 50 hours or more.

Figure 3:
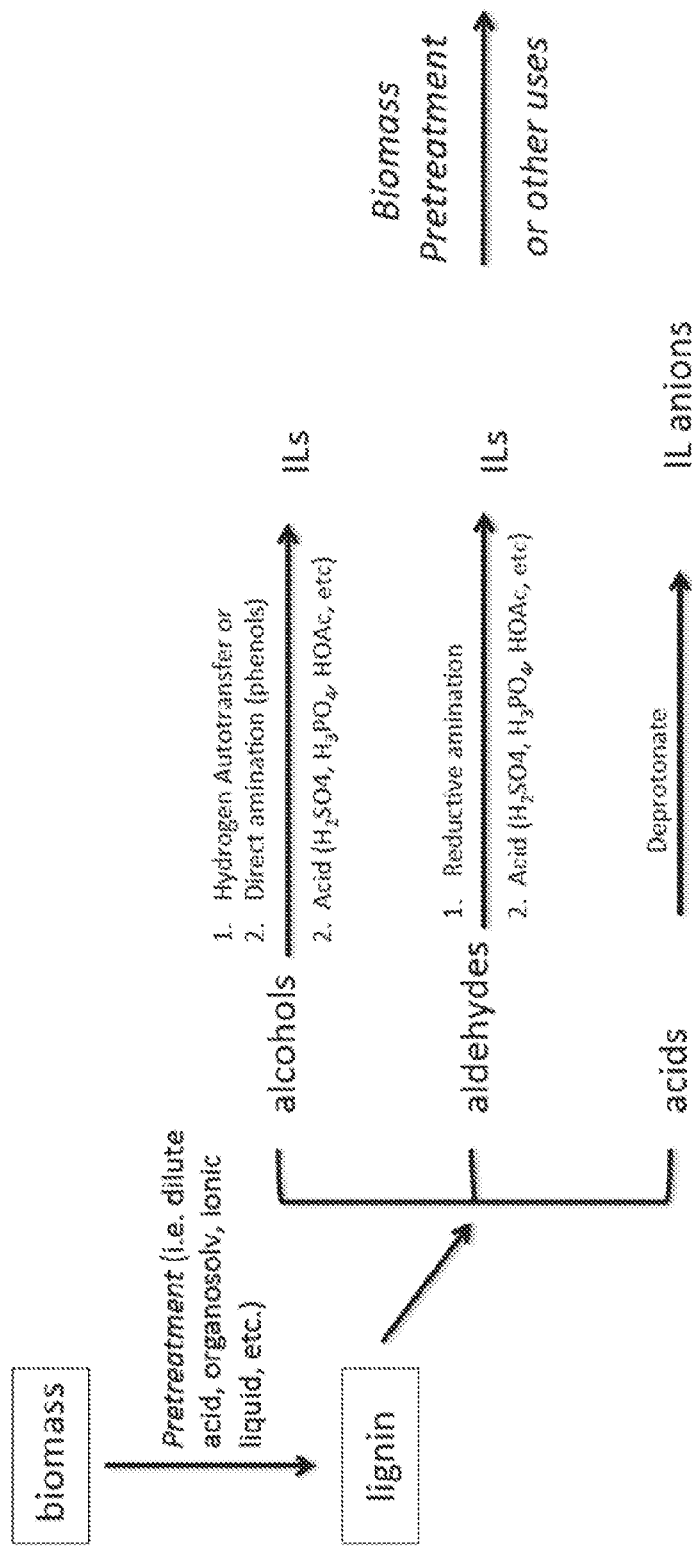
FIG. 3 depicts a methodology for producing ionic liquids from lignin. Lignin derived alcohols and aldehydes can be used to generate amines and subsequently cations via amination and salt formation. Carboxylic acids derived from lignin can be deprotonated to form anions. The ionic liquids thus formed, or combinations thereof, can be used for biomass pretreatment and other applications.

In some embodiments, ionic liquids of the present invention are prepared by the method outlined in FIG. 3. In some embodiments ionic liquids of the present invention are prepared by: contacting a lignin starting material with a depolymerization agent to depolymerize the lignin and form a mixture of aldehyde containing compounds; contacting the mixture of aldehyde containing compounds with an amine under conditions suitable to convert the mixture of aldehyde containing compounds to a mixture of amine containing compounds; and contacting the mixture of amine containing compounds with a mineral acid under conditions suitable conditions to form an amine salt, thereby preparing an ionic liquid. In some cases, the ionic liquids thus prepared are room temperature ionic liquids. In some cases, the ionic liquids thus prepared are liquid at less than about 100° C. under atmospheric pressure. In some cases, the method of extracting the lignin from the lignin starting material (e.g., lignocellulosic biomass) includes contacting the lignin starting material with an ionic liquid prepared by the foregoing method under conditions suitable to extract the lignin. In some cases, the contacting with an ionic liquid extracts and depolymerizes the lignin. In some embodiments, ionic liquids thus prepared can be utilized for biomass pretreatment. For example, treatment of biomass in a closed-loop system in which biomass is treated to generate ionic liquids which are then utilized to treat biomass to generate ionic liquids and/or other useful products.

All patents, patent applications, and other publications cited in this application are incorporated by reference in the entirety for all purposes.

V. Examples

All solvents and chemicals were reagent grade and used without purification. NMR Spectra were obtained on a Bruker 600 MHz instrument equipped with a cryoprobe. $^1$H NMR spectra were calibrated to TMS ($\delta$=0.00) and $^{13}$C NMR spectra were calibrated to DMSO ($\delta$=39.5). Low-resolution mass spectrometry was performed on an Agilent 6890 GC equipped with an Agilent 5973 mass detector.

Example 1: Production of Ionic Liquids from Lignin a. Depolymerization

Lignin is depolymerized by methods known in the art (See. e.g., Pandey, 2011). Briefly, 40 g of lignin is contacted with 80 g of $CuSO_4.5H_2O$ and 70 g of NaOH in 400 g of H₂O for 5 hours at 160° C. to yield low molecular weight (e.g., monomer, dimer, trimer, etc.) aromatic aldehydes (Pearl, 1942).

b. Reductive Amination

Aromatic aldehydes are converted to diethylamines via reductive amination by methods known in the art (See, e.g., Abdel-Magid, 1996). Briefly, 12.9 mL (1.2 equiv.) of diethylamine is added to a stirred solution of 10 g of the aldehydes obtained in step (a) in 260 mL 1,2-dichloroethane or acetonitrile. The mixture is stirred for 5 min. Optionally, glacial acetic acid (1 equiv.) is added to facilitate conversion of the amino-alcohol adduct to the iminium species, which is reduced in the next step. The mixture is cooled to 0° C. Sodium triacetoxyborohydride (30.9 g, 1.4 equiv.) is added portion-wise, and the mixture is stirred at room temperature overnight. The solution is quenched by adding aq. 1M HCl and the amine product is thus drawn in the aqueous phase. The organic impurities are removed by washing with CH₂Cl₂. The pH of the aqueous phase is raised to approximately 10.3 by addition of 1M NaOH, and the product is extracted with EtOAc (2×). The combined organic layers are dried over MgSO₄, and concentrated to afford the amines.

c. Salt Formation 32.6 mL of 2M H₂SO₄ (1 equiv.) in MeOH is added to a stirred solution containing 10 g of the amines obtained in step (b) (~1 equiv.) in MeOH (45 mL) at 0°. Methanol is evaporated under vacuum and the ionic liquid is obtained in quantitative yield.

Example 2: Reductive Amination of Lignoaldehydes a. N-Ethyl-N-(furan-2-ylmethyl)ethanamine (1)

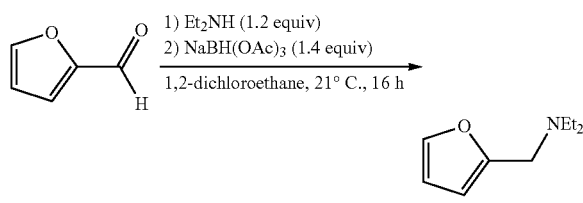

General Protocol (Abdel-Magid, (1996)):

To a stirred solution of furfural (10.0 g, 1 equiv.) in 1,2-dichloroethane or acetonitrile (260 mL) is added diethylamine (12.9 mL, 1.2 equiv.) and the mixture is stirred for 5 min. Optionally, glacial acetic acid (1 equiv.) can be added to facilitate the conversion of the amino-alcohol adduct to the iminium species, which is reduced in the next step. The mixture is cooled to 0° C. Sodium triacetoxyborohydride (30.9 g, 1.4 equiv.) is added portion-wise, and the mixture is stirred at room temperature overnight. The solution is quenched by adding aq. 1M HCl and the amine product is thus drawn in the aqueous phase. The organic impurities are removed by washing with CH2Cl₂. The pH of the aqueous phase is raised to approximately 10.3 by addition of 1M NaOH, and the product is extracted with EtOAc (2×). The combined organic layers are dried over MgSO₄, and concentrated to afford the amine in 56% yield. m/z [M⁺] Obsd. 153.1 Calcd. 153.12 for C₉H₁₇NO ¹H NMR (DMSO-d₆) 0.96 (t, 6H), 2.41 (q, 4H), 3.56 (s, 2H), 6.22 (s, 1H) 6.36 (s, 1H) 7.53 (s, 1H).

b. 4-((Diethylamino)methyl)phenol (2)

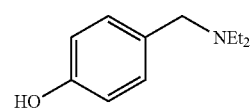

Following the general protocol for reductive amination, the procedure was performed with 10.0 g (1 eq) of p-hydroxybenzaldehyde, compound 2 was obtained in 77% yield. m/z [M⁺] Obsd. 179.1 Calcd. 179.13 for C₉H₁₅NO ¹H NMR (DMSO-d₆) 0.93 (t, 6H), 2.40 (q, 4H), 3.38 (s, 2H), 6.70 (d, 2H), 7.07 (d, 2H).

c. N-Ethyl-N-(3-methoxybenzyl)ethanamine (3)

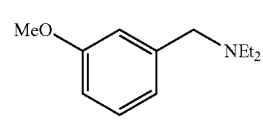

Following the general protocol for reductive amination, the procedure was performed with 10.0 g (1 eq) of 3-methoxybenzaldehyde, compound 3 was obtained in 89% yield. m/z [M⁺] Obsd. 193.1 Calcd. 193.15 for C₁₂H₁₉NO ¹H NMR (DMSO-d₆) 0.94 (t, 6H), 2.42 (q, 4H), 3.46 (s, 2H), 3.71 (s, 3H) 6.76 (d, 1H), 6.86 (m, 2H) 7.18 (t, 1H).

d. 2-((Diethylamino)methyl)benzene-1,4-diol (4)

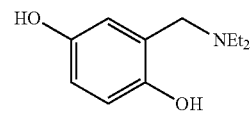

Following the general protocol for reductive amination, the procedure was performed with 10.0 g, (1 eq) of 2,5-dihydroxybenzaldehyde, compound 4 was obtained in 83% yield. m/z [M⁺] Obsd. 195.1 Calcd. 195.13 for C₁₁H₁₇NO₂ ¹H NMR (DMSO-d₆) 1.00 (t, 6H), 2.53 (q, 4H), 3.46 (s, 2H), 6.49 (m, 3H).

e. 4-((Diethylamino)methyl)-2,6-dimethoxyphenol (5)

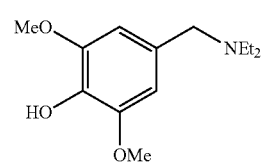

Following the general protocol for the reductive amination, the procedure was performed with 10.0 (1 eq) of syringaldehyde, compound 5 was obtained in 25% yield.

m/z [M+] Obsd. 239.1 Calcd. 239.15 for $C_{13}H_{21}NO_3$ $^1$H NMR (DMSO-$d_6$) 0.97 (t, 6H), 2.45 (q, 4H), 3.42 (s, 2H), 3.73 (s, 6H) 6.55 (s, 2H).

f. (E)-N,N-Diethyl-3-phenylprop-2-en-1-amine (6)

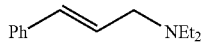

6

Following the general protocol for the reductive amination, the procedure was performed with 10.0 g (eq) of trans-cinnamaldehyde, compound 6 was obtained in 94% yield. m/z [M+] Obsd. 189.1 Calcd. 189.15 for $C_{13}H_{19}N$ $^1$H NMR (DMSO-$d_6$) 0.99 (t, 6H), 2.50 (q, 4H), 3.19 (s, 2H), 6.29 (m, 1H), 6.53 (m, 1H), 7.23 (m, 1H), 7.31 (m, 2H), 7.42 (m, 2H).

g. 4-((Diethylamino)methyl)-2-methoxyphenol (7)

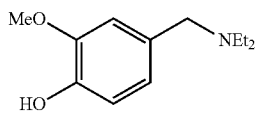

7

Following the general protocol for the reductive amination, the procedure was performed with 10.0 g (1 eq) of vanillin, compound 7 was obtained in 81% yield. m/z [M+] Obsd. 209.1 Calcd. 209.14 for $C_{12}H_{19}NO_2$ $^1$H NMR (DMSO-$d_6$) 1.04 (t, 6H), 2.54 (q, 4H), 3.52 (s, 2H), 3.79 (s, 3H), 6.75 (m, 2H), 6.91 (m, 1H).

h. N-Benzyl-N-ethylethanamine (8)

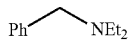

8

Following the general protocol for the reductive amination, the procedure was performed with 10.0 g (1 eq) of benzaldehyde, compound 8 was obtained in 59% yield. m/z [M+] Obsd. 163.2 Calcd. 163.14 for $C_{11}H_{17}N$ $^1$H NMR (DMSO-$d_6$) 0.96 (t, 6H), 2.44 (q, 4H), 3.51 (s, 2H), 7.21 (m, 1H) 7.29 (m, 4H).

i. 5-((Diethylamino)methyl)-2-methoxyphenol (9)

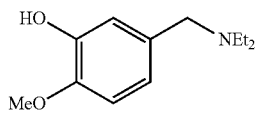

9

Following the general protocol for the reductive amination, the procedure was performed with 10.0 g (1 eq) of 3-hydroxy-4-methoxybenzaldehyde, compound 9 was obtained in 95% yield. m/z: [M+] Obsd. 209.1 Calcd. 209.14 for $C_{12}H_{19}NO_2$ $^1$H NMR (DMSO-$d_6$) 0.95 (t, 6H), 2.42 (q, 4H), 3.36 (s, 2H), 3.73 (s, 3H), 6.64 (d, 1H), 6.75 (s, 1H), 6.81 (d, 1H).

Example 3: Formation of the Ionic Liquids Via Protonation a. N-Ethyl-N-(furan-2-ylmethyl)ethanamine, $H_2SO_4$ salt (1a)

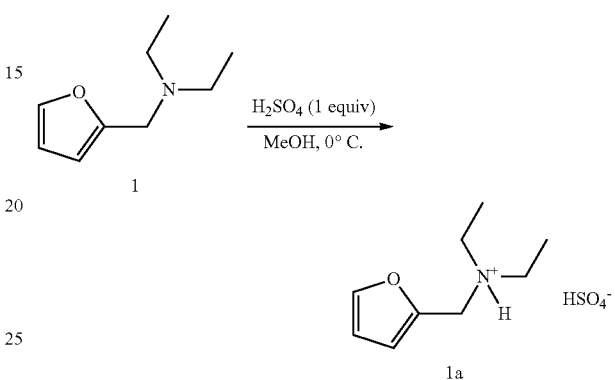

General Protocol:

To a stirred solution of 1 (10.0 g, 1 equiv.) in MeOH (45 mL) at 0° C. is added $H_2SO_4$ (2 M in MeOH, 32.6 mL, 1 equiv.). Methanol is evaporated under vacuum and the ionic liquid 1a is obtained in quantitative yield. All the hydrogen sulfate ionic liquids described below are prepared by this method. $^1$H NMR (DMSO-$d_6$) 1.25 (t, 6H), 3.08 (q, 4H), 4.43 (s, 2H), 6.58 (s, 1H) 6.78 (s, 1H) 7.85 (s, 1H). $^{13}$C NMR (DMSO-$d_6$) 8.8 (2C), 46.8 (2C), 52.9, 111.2, 114.3, 144.0, 145.1.

b. N-Ethyl-N-(furan-2-ylmethyl)ethanamine, $H_3PO_4$ salt (1b)

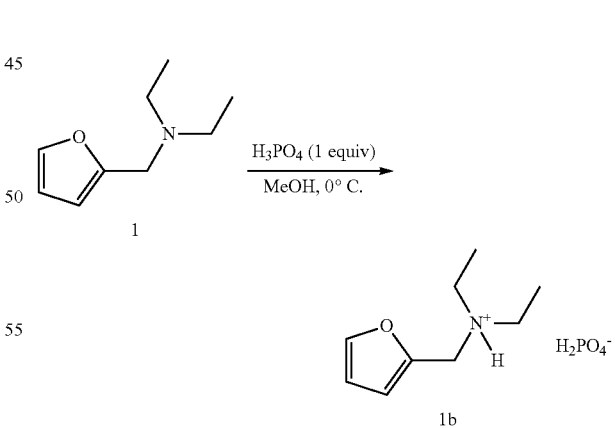

General Protocol:

To a stirred solution of 1 (10.0 g, 1 equiv.) in MeOH (45 mL) at 0° C. is added $H_3PO_4$ (2 M in MeOH, 32.6 mL. 1 equiv.). Methanol is evaporated under vacuum and the ionic liquid 1b is obtained in quantitative yield. All the dihydrogen phosphate ionic liquids described below are prepared by this method. $^1$H NMR (DMSO-$d_6$) 1.07 (t, 6H), 2.61 (q, 4H), 3.85 (s, 2H), 6.44 (s, 2H), 7.63 (s, 1H) $^{13}$C NMR (DMSO-$d_6$) 10.8 (2C), 46.3 (2C), 47.5, 110.3, 110.5, 143.0, 149.6.

c. 4-((Diethylamino)methyl)phenol, $H_2SO_4$ salt (2a)

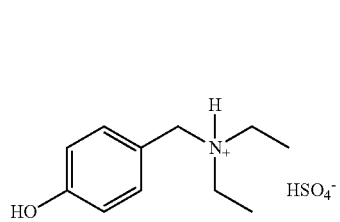

2a $^1$H NMR (DMSO-$d_6$) 1.22 (t, 6H), 3.05 (q, 4H), 4.18 (s, 2H), 6.84 (d, 2H), 7.33 (d, 2H); $^{13}$C NMR (DMSO-$d_6$) 8.5 (2C), 45.7 (2C), 53.0, 115.6 (2C), 128.0, 132.5 (2C), 158.4.

d. 4-((Diethylamino)methyl)phenol, $H_3PO_4$ salt (2b)

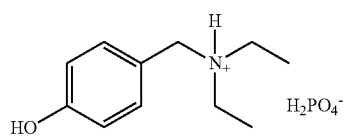

2b $^1$H NMR (DMSO-$d_6$) 1.07 (t, 6H), 2.67 (q, 4H), 3.73 (s, 2H), 6.76 (d, 2H), 7.21 (d, 2H); $^{13}$C NMR (DMSO-$d_6$) 9.9 (2C), 45.4 (2C), 55.2, 115.2 (2C), 129.4, 131.1 (2C), 157.3.

e. N-Ethyl-N-(3-methoxybenzyl)ethanamine, $H_2SO_4$ salt (3a)

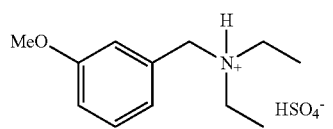

3a $^1$H NMR (DMSO-$d_6$) 1.23 (t, 6H), 3.09 (q, 4H), 3.81 (s, 3H), 4.29 (s, 2H), 7.03 (m, 1H), 7.12 (m, 2H) 7.39 (m, 1H); $^{13}$C NMR (DMSO-$d_6$) 8.4 (2C), 46.1 (2C), 55.1, 55.2, 115.0, 116.3, 122.9, 130.0, 131.7, 159.5.

f. N-Ethyl-N-(3-methoxybenzyl)ethanamine, $H_3PO_4$ salt (3b)

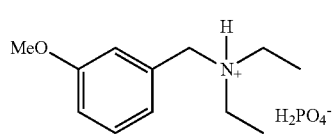

3b $^1$H NMR (DMSO-$d_6$) 1.07 (t, 6H), 2.69 (q, 4H), 3.73 (s, 3H), 3.83 (s, 2H), 6.86 (m, 1H), 7.04 (m, 2H) 7.23 (m, 1H); $^{13}$C NMR (DMSO-$d_6$) 9.8 (2C), 45.8 (2C), 55.3, 55.8, 113.9, 115.3, 122.2, 129.7, 136.5, 159.6.

g. 2-((Diethylamino)methyl)benzene-1,4-diol, $H_2SO_4$ salt (4a)

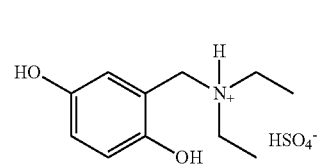

4a $^1$H NMR (DMSO-$d_6$) 1.23 (t, 6H), 3.08 (q, 4H), 4.12 (s, 2H), 6.73 (m, 1H), 6.77 (m, 2H); $^{13}$C NMR (DMSO-$d_6$) 8.6 (2C), 46.6 (2C), 52.9, 55.8, 116.2, 117.1, 117.6, 118.4, 148.9, 149.8.

h. 2-((Diethylamino)methyl)benzene-1,4-diol, $H_3PO_4$ salt (4b)

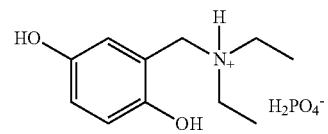

4b $^1$H NMR (DMSO-$d_6$) 1.11 (t, 6H), 2.73 (q, 4H), 3.80 (s, 2H), 6.60 (m, 2H), 6.68 (m, 1H); $^{13}$C NMR (DMSO-$d_6$) 10.1 (2C), 45.9 (2C), 53.2, 115.6, 116.2, 116.7, 120.9, 149.5, 149.8.

i. 4-((Diethylamino)methyl)-2,6-dimethoxyphenol, $H_2SO_4$ salt (5a)

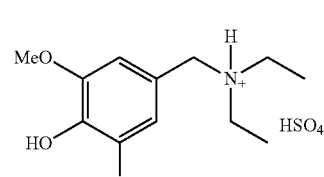

5a $^1$H NMR (DMSO-$d_6$) 1.23 (t, 6H), 3.07 (q, 4H), 3.79 (s, 6H), 4.16 (s, 2H), 6.81 (s, 2H); $^{13}$C NMR (DMSO-$d_6$) 8.5 (2C), 45.8 (2C), 53.0, 56.2 (2C), 108.4 (2C), 120.1, 136.5, 148.0 (2C).

j. 4-((Diethylamino)methyl)-2,6-dimethoxyphenol, $H_3PO_4$ salt (5b)

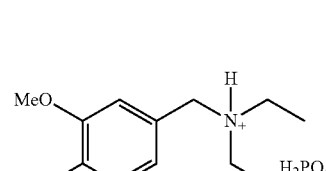

5b

¹H NMR (DMSO-d₆) 1.07 (t, 6H), 2.66 (q, 4H), 3.69 (s, 2H), 3.75 (s, 6H), 6.73 (s, 2H); ¹³C NMR (DMSO-d₆) 10.1 (2C), 45.5 (2C), 56.1 (2C), 56.4, 107.0 (2C), 125.9, 135.0, 147.9 (2C).

k. (E)-N,N-Diethyl-3-phenylprop-2-en-1-amine, H₂SO₄ salt (6a)

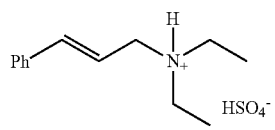

¹H NMR (DMSO-d₆) 1.24 (t, 6H), 3.15 (q, 4H), 3.89 (s, 2H), 6.37 (m, 1H), 6.92 (d, 1H), 7.34 (m, 1H), 7.40 (m, 2H), 7.54 (m, 2H); ¹³C NMR (DMSO-d₆) 8.9 (2C), 46.3 (2C), 52.9, 118.1, 126.8 (2C), 128.6, 128.7 (2C), 135.4, 138.4.

l. (E)-N,N-Diethyl-3-phenylprop-2-en-1-amine, H₃PO₄ salt (6b)

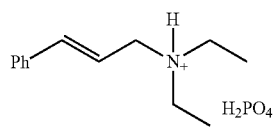

¹H NMR (DMSO-d₆) 1.09 (t, 6H), 2.74 (q, 4H), 3.47 (s, 2H), 6.39 (m, 1H), 6.65 (d, 1H), 7.21 (m, 1H), 7.31 (m, 2H), 7.44 (m, 2H); ¹³C NMR (DMSO-d₆) 9.9 (2C), 45.8 (2C), 53.6, 123.0, 126.7 (2C), 128.0, 128.7 (2C), 134.9, 136.3.

m. 4-((Diethylamino)methyl)-2-methoxyphenol, H₂SO₄ salt (7a)

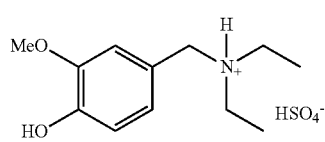

¹H NMR (DMSO-d₆) 1.15 (t, 6H), 2.97 (q, 4H), 3.74 (s, 3H), 4.08 (s, 2H), 6.77 (d, 1H), 6.85 (d, 1H), 7.07 (s, 1H): ¹³C NMR (DMSO-d₆) 8.5 (2C), 45.7 (2C), 55.3, 114.8, 115.5, 121.0, 123.8, 147.5, 147.7.

n. 4-((Diethylamino)methyl)-2-methoxyphenol, H₃PO₄ salt (7b)

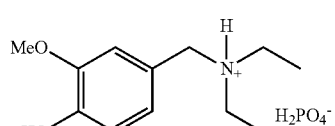

¹H NMR (DMSO-d₆) 1.05 (t, 6H), 2.71 (q, 4H), 3.73 (s, 2H), 6.78 (m, 2H), 7.08 (s, 1H); ¹³C NMR (DMSO-d₆) 9.6 (2C), 45.4 (2C), 55.7, 55.8, 114.2, 115.4, 122.8, 124.8, 146.8, 147.8.

o. N-Benzyl-N-ethylethanamine, H₂SO₄ salt (8a)

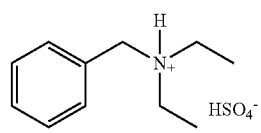

¹H NMR (DMSO-d₆) 1.15 (t, 6H), 2.87 (q, 4H), 4.05 (s, 2H), 7.37-7.42 (m, 3H) 7.49 (d, 2H) ¹³C NMR (DMSO-d₆) 9.4 (2C), 46.0 (2C), 55.5, 128.4, 128.6 (4C), 130.2.

p. N-Benzyl-N-ethylethanamine, H₃PO₄ salt (8b)

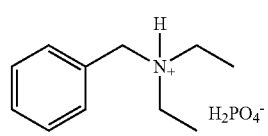

¹H NMR (DMSO-d₆) 1.10 (t, 6H), 2.72 (q, 4H), 3.87 (s, 2H), 7.33 (m, 1H) 7.37 (t, 2H), 7.47 (d, 2H) ¹³C NMR (DMSO-d₆) 9.9 (2C), 45.8 (2C), 55.8, 127.9, 128.5 (2C), 129.8 (2C), 135.2.

q. 5-((Diethylamino)methyl)-2-methoxyphenol, H₂SO₄ salt (9a)

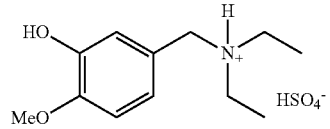

¹H NMR (DMSO-d₆) 1.18 (t, 6H), 2.94 (m, 4H), 3.40 (s, 2H) 3.79 (s, 3H), 6.89 (d, 1H) 6.92 (s, 1H) 6.96 (d, 1H) ¹³C NMR (DMSO-d₆) 8.9 (2C), 45.7 (2C), 52.8, 55.6, 112.1 (2C), 117.6, 121.7, 146.5, 148.2.

r. 5-((Diethylamino)methyl)-2-methoxyphenol, H₃PO₄ salt (9b)

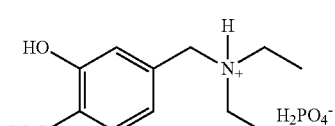

$^1$H NMR (DMSO-d$_6$) 1.04 (t, 6H), 2.60 (m, 4H), 3.60 (s, 2H) 3.75 (s, 3H), 6.74 (d, 1H) 6.86 (m, 2H) $^{13}$C NMR (DMSO-d$_6$) 10.5 (2C), 45.8 (2C), 55.6, 55.8, 111.9 (2C), 116.6, 120.0, 146.4, 147.1.

REFERENCES

Pearl, I A *J. Am. Chem. Soc.*, 64 (6), pp 1429-1431, (1942).
Liu S. *Process of lignin oxidation in ionic liquids coupled with separation*. RSC Advances Online Advance Manuscript doi:10.1039/C3RA40391B, (2013).
Pu et al., *J Wood Chem Technol*, 27, 23-33, (2007).
Binder J B *Biomass Bioenergy*, 33, 1122-1130, (2009).
Lee S H *Biotechnol Bioeng*, 102, 1368-1376, (2009).
Pandey et al., *Chem. Eng. Technol.* 34, No. 1, 29-41, (2011).
C. Li, Q. Wang and Z. K. Zhao, *Green Chem.*, 10, 177-182, (2008).
Wu et al., Ind. Eng. Chem. Res., 33, 718 (1994).
Kahl et al., *Aniline*, Wiley-VCH Verlag GmbH & Co. KGaA, Weinheim p. 6 section 3.2.3
"Amination of Phenol" DOI: 10.1002/14356007.a02 303, (2005).
Watson, A J A. et al., *J. Org. Chem.*, 76, 2328-2331, (2011).
Ghosh R. *J. Org Chem*, 76, 20, 8508-8512, (2011).
Kumar et al., *Green Chem*, 14, 3410, (2012).
NABC: *Understanding the mechanisms of lignin depolymerization*, (2012).
Chiappe. C. *Green Chem.*, 13, 1437-1441, (2011).
M. Kleen, G. Gellerstedt, *J. Anal. Appl. Pyrolysis*, 19, 139, (1991).
Q. Xiang. Y. Y. Lee. *Appl. Biochem. Biotechnol.*, 84-86, 153, (2000).
Sommer, H Z et al., Alkylation of Amines. *Edgewood Arsenal Technical Report*, (1969).
Abdel-Magid, A. F.; Carson, K. G.; Harris, B. D.; Maryanoff, C. A.; Shah, R. D. *J. Org. Chem*, 61, 3849-3862, (1996).
Holbrey el al., *Green Chem.*, (2002).
M. P. Masingale et al., *Bioresources*, 4 (3), 1139, (2009).
Villar, A. Caperos, F. Garcia-Ochoa, *J. Wood Chem. Technol.*, 17, 259, (1997).
Lu, el al., *Tetrahedron Letters*, 43, 8617, (2002).
Abdel-Magid, et al., *Org. Process Res. Dev.*, 10(5):971-1031, (2006).
Rossi, et al., *J Org Chem*, 37, 22, 3570, (1972).

Example 4: Formation of the Ionic Liquids Via Protonation

I. Introduction

Room temperature ionic liquids (ILs) are commonly defined as molten salts with melting points less than 100° C., and many ILs are considered environmentally friendly solvents for a variety of industrial applications. Their ionic, non-coordinating nature allows ILs to dissolve unique combinations of organic and inorganic compounds, facilitating diverse types of chemical transformation and separation processes (1, 2). ILs are often immiscible with organic solvents and thus provide non-aqueous alternatives for biphasic reaction systems, such as those involving homogeneous catalysts (3). In many cases, ILs are considered for "green chemistry" due to their low vapor pressures, high thermal stabilities and relative non-toxicity. As such they are emerging as important materials for drug delivery (4), lubrication (5) and electrolytes (6) including those for lithium ion (7) and lithium sulfur batteries (8). ILs have also found utility as heat transfer media for solar thermal systems (9), carbon capture (10) and biodiesel production (1). Among the industrial applications with highest potential volume requirements of these remarkable solvents is the processing of lignocellulosic biomass, and subsequent fermentation, to produce specialty and commodity chemicals including advanced biofuels. (12-15).

Lignin and polysaccharides found in plant cell walls represent the two largest components of biomass on Earth, and it has been estimated that the United States can produce approximately 1.3 billion tons of lignocellulosic biomass per year (16). Lignin is a heterogeneous polymer that constitutes 20-30% of dry biomass in woody plants (17) and 15-20% in grasses (18). The monomeric composition of lignin comprises three primary phenylpropane units, p-coumaryl alcohol, coniferyl alcohol and sinapyl alcohol, though this varies between species and the methods used for its extraction. Cellulose, a crystalline polymer of D-glucose, is the principal component of biomass, accounting for approximately 40-50% of the dry biomass in woody plants and grasses (18, 19). Hemicellulose is a heterogeneous polymer of pentose and hexose sugars; mannose predominates in woody plants, and xylose is primarily found in grasses. The composition of hemicellulose also varies by species, and accounts for approximately 25% of the dry biomass of woody plants (20) and approximately 30% of grasses (18).

Pretreatment of lignocellulosic biomass has been achieved under a variety of condition including steam explosion, acidic and alkaline methods, and has been review extensively (21, 22). While several methods can provide high yields of glucose and xylose, downstream fermentation of these sugars are often confounded by toxic byproducts (23). Due to their ability to selectively remove lignin and hemicellulose from biomass, effectively providing pure decrystallized cellulose for enzymatic hydrolysis, certain ILs are exceptional pretreatment solvents (24-26). The most well studied ILs are currently considered expensive for large-scale biomass processing, typically require multistep syntheses, and are primarily derived from non-renewable resources. For example, imidazole and pyridine, two of the best cation moieties for biomass pretreatment, are prepared industrially by the Radziszewski (27) and Chichibabin (28) condensation reactions, respectively. The starting materials for these syntheses include glyoxal and acetaldehyde, both of which are produced from ethylene, which can be obtained from petroleum cracking and/or hydraulic fracturing.

Figure 11:
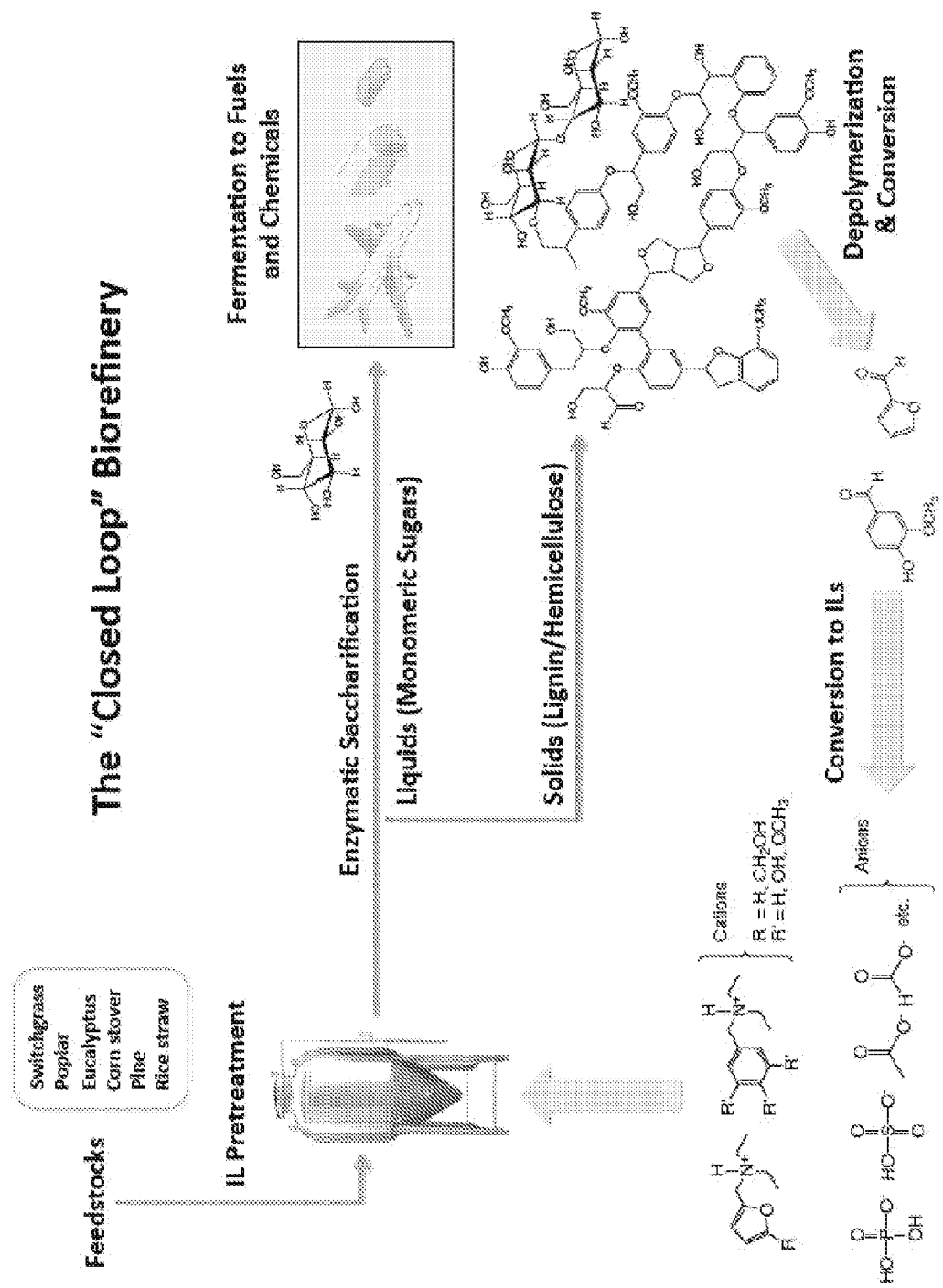
FIG. 11 depicts a hypothetical process flow for a closed loop bio-refinery using ionic liquids (ILs) derived from lignocellulosic biomass.

Imidazolium and other cations containing aromatic moieties have been shown to improve lignin dissolution of wood (29, 30). With this in mind we turned our attention to the use of lignin- and hemicellulose-derived compounds as potential candidates for IL synthesis. These polymers represent inexpensive and abundant waste streams from a variety of biomass processing industries including textiles, pulp/paper and biofuels. Chemical processes to produce ionic liquids directly from biomass could enable bio-refineries to operate at lower costs by utilizing large volume waste streams (FIG. 11). Critical to development of this "closed loop" biorefinery concept is the controlled depolymerization of lignin and hemicellulose. Depending on the methods employed, it is possible to direct depolymerization towards desired product streams, such as aromatic aldehydes, acids and alcohols (31-33). For example, classic oxidative methods involving CuSO4 with NaOH yield hydroxyl- and methoxyl-substituted aromatic aldehydes (34), particularly vanillin and syringaldehyde. A similar catalytic system, employing CuSO4 with quaternary ammonium and imidazolium dimethylphosphate ILs, has been shown to convert approximately 30% of lignin to aldehydes (35). Pyrolysis of lignin primarily produces aldehydes and phenols (3). Biological treatment of lignin by fungi of the genus Pleurotus has been shown to produce p-anisaldehyde as the dominant aromatic metabolite found in the culture broth (36). Aldehydes such as furfural and hydroxymethylfurfural (HMF) can be derived in high yields from cellulose, hemicellulose and raw biomass (37). Ionic liquid pretreatment of lignocellulosic biomass itself results in small aromatics from lignin breakdown. These small aromatics, and other lignin breakdown products, can be converted into renewable ILs as described herein.

Figure 12:
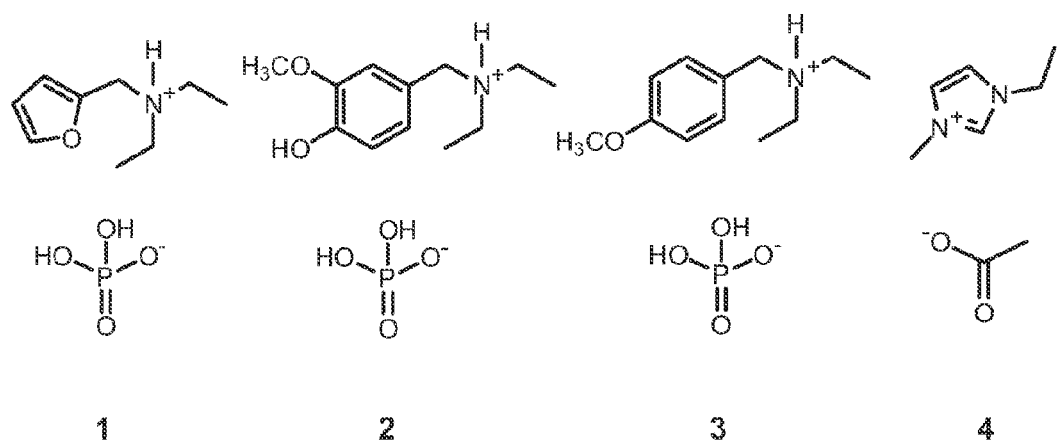
FIG. 12 depicts exemplary lignin and hemicellulose derived renewable ILs. [Fur][H$_2$PO$_4$]. [Van][H$_2$PO$_4$] and [p-Anis][H$_2$PO$_4$] were prepared from furfural, vanillin and p-anisaldehyde, respectively. IL 4 is [C$_2$mim][OAc].

Described herein is the first synthesis and evaluation of ILs from these targeted lignin- and hemicellulose-derived compounds. Specifically, reductive amination chemistry was used to produce tertiary amines that were protonated with phosphoric acid to form the desired ILs. Dihydrogenphosphate containing ILs (1-3), were prepared from furfural, vanillin and p-anisaldehyde, respectively. Combinations of computational and experimental methods were used to compare these compounds to 1-ethyl-3-methylimidazolium acetate, [C$_2$mim][OAc] (4), an ionic liquid that has been well studied owing to its efficacy in biomass pretreatment (FIG. 12).

II. Results

Synthesis of Ionic Liquids:

Reductive amination of aldehydes derived from lignin and hemicellulose proceeded in excellent yields. A solution of the aldehyde was treated with diethylamine and sodium triacetoxyborohydride in 1,2-dichlorethane (38). A two-step acid/base workup provided the desired tertiary amine product without requiring any additional purification.

Furfural was first selected for reductive amination, as it is readily obtained from the acid-catalyzed dehydration of pentose sugars commonly found in hemicellulose. Its tertiary amine derivative, N-ethyl-N-(furan-2-ylmethyl)ethanamine, was obtained in 82% yield. Vanillin and p-anisaldehyde were selected as lignin derived aldehydes, and reductive amination provided their tertiary amine derivatives, 4-((diethylamino)methyl)-2-methoxyphenol and N-ethyl-N-(4-methoxybenzyl)ethanamine in 87% and 94% yield, respectively. The resulting amines were converted to ILs [Fur][H$_2$PO$_4$] (1), [Van][H$_2$PO$_4$] (2) and [p-Anis][H$_2$PO$_4$] (3) via stoichiometric addition of phosphoric acid in nearly quantitative yields (Scheme 1).

Scheme 1

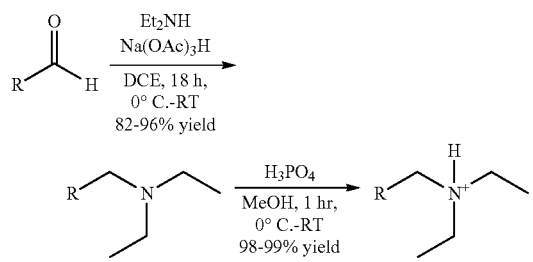

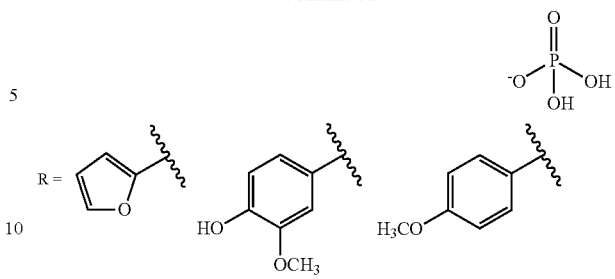

In all cases, $^1$H NMR showed deshielding of methylene and methyl protons of the newly formed alkyl ammonium dihydrogen phosphate ILs, as compared to those observed in the respective tertiary amines. For example, the methylene protons of the tertiary amine derived from furfural migrated downfield from δ=2.41 ppm to δ=2.79 ppm (q, 4H, J=8 Hz) and from δ=3.56 ppm to δ=4.09 ppm (s, 2H) upon conversion to [Fur][H$_2$PO$_4$]. A similar trend was observed for the equivalent protons of the methyl groups, shifting from δ=0.99 ppm in the amine to δ=1.19 ppm (t, 6H, J=8 Hz) in the IL. Upon formation of [Fur][H$_2$PO$_4$] from the tertiary amine, $^{13}$C NMR revealed shielding effects on methyl carbon atoms, which shifted upfield from δ=11.9 in the amine to δ=9.7 ppm in the resulting IL. A slight shielding of the methylene carbons in the α position were also observed when converting the amine δ=45.9 ppm (2C) and δ=54.8 ppm (1C) to the IL δ=45.3 ppm (2C) and δ=54.6 ppm (1C). Similar chemical shift trends were observed for [Van][H$_2$PO$_4$] and [p-Anis][H$_2$PO$_4$], when compared to their respective amines derived from vanillin and p-anisaldehyde. In total, these results compared well to model tertiary amines (39).

In addition to being among the most abundant representative aldehydes of chemically and biologically depolymerized lignin, respectively, [Van][H$_2$PO$_4$] and [p-Anis][H$_2$PO$_4$] were also selected based on their subtle differences in polarity and substituent effects. The polarity of an IL has been correlated with its ability to solubilize both lignin (40, 41) and cellulose (42, 43). Hydroxyl and methoxyl groups activate aromatic ring systems and therefore [Van][H$_2$PO$_4$] and [p-Anis][H$_2$PO$_4$] were used to dissect the role of these substituents on the cations' relative acidity, and their affect on biomass pretreatment.

Compositional Analysis of Raw and IL-Pretreated Switchgrass:

Compositional analysis of cellulose, hemicellulose and lignin was performed directly on the untreated (raw) switchgrass (SG), and glucan and lignin values are in good agreement with previously published values (18, 44). The raw biomass contains 34.7% glucan, 21.8% xylan and 19.3% lignin (Table 2). Approximately 22% of the biomass could not be accounted for and this is likely the result of a combination of sampling error, and/or the presence of extractive compounds.

TABLE 2

Composition Analysis of IL-pretreated and Raw Switchgrass

| IL Pretreatment | Solid recovery, % | Glucan, % | Xylan, % | Arabinan, % | Lignin, % | Xylan removal, % | Lignin removal, % |
|---|---|---|---|---|---|---|---|
| [Fur][H$_2$PO$_4$] | 62.8 ± 1.1 | 52.5 ± 0.7 | 17.8 ± 0.6 | 2.7 ± 0.1 | 24.6 ± 0.6 | 48.8 | 20.0 |
| [Van][H$_2$PO$_4$] | 77.9 ± 0.9 | 41.9 ± 0.4 | 23.8 ± 0.3 | 3.1 ± 0.1 | 23.8 ± 0.3 | 33.9 | 3.9 |
| [p-Anis][H$_2$PO$_4$] | 56.7 ± 1.7 | 54.5 ± 0.9 | 18.7 ± 0.3 | 3.0 ± 0.1 | 19.4 ± 0.9 | 51.4 | 43.0 |
| [C$_2$mim][OAc] | 58.0 ± 1.2 | 55.2 ± 0.5 | 20.8 ± 1.2 | 3.9 ± 0.1 | 15.8 ± 0.1 | 44.8 | 52.4 |
| Raw switchgrass | N/A | 34.7 ± 1.3 | 21.8 ± 0.5 | 2.6 ± 0.4 | 19.3 ± 1.5 | N/A | N/A |

± Indicates standard deviation

Switchgrass was pretreated with ILs synthesized from lignin and hemicellulose as well as the well-known commercial IL used in pre-treatment of biomass, [C$_2$mim][OAc], at 160° C., and subsequent compositional analysis was performed on biomass regenerated from reactions using water as the antisolvent. As expected, pretreatment increased the percent by mass of cellulose through the solubilization of lignin and hemicellulose. The benchmark IL for biomass pretreatment, [C$_2$mim][OAc] provided results consistent with previous studies, showing 58.0% biomass recovery, of which 55.2% was glucan, 20.8% xylan and 15.8% was lignin. This equates to 44.8% xylan and 52.4% lignin removal, respectively.

Of the lignin-based ILs tested, [Van][H$_2$PO$_4$] provided the highest solid recovery (77.9%) but also performed poorest in terms of xylan and lignin removal, with 33.9% and 3.9% respectively. It is hypothesized that since [Van][H$_2$PO$_4$] is the most polar IL, it is least suitable for lignin removal. The least polar biomass-derived IL, [p-Anis][H$_2$PO$_4$], showed far greater xylan and lignin removal, 51.4% and 43.0% respectively, with total solid recovery of 56.7%. When comparing the monomeric sugar yields between [Van][H$_2$PO$_4$] and [p-Anis][H$_2$PO$_4$] it appears that [p-Anis][H$_2$PO$_4$] is a more promising candidate, as it provided 73.2% of the recovered biomass as glucan or xylan, as compared to these combined sugar yields of [Van][H$_2$PO$_4$], being approximately 65.7%.

Compositional analysis of switchgrass pretreated with [Fur][H$_2$PO$_4$] showed 62.8% solid recovery, of which 52.5% was glucan and 17.8% was xylan. Significant xylan removal (48.8%) and lignin removal (20%) was observed for furfural derived IL.

Performance Evaluation of Renewable ILs:

From the compositional analysis, it was clear that 91-95% and 49-85% of the samples' glucan and xylan were respectively recovered in the solids. To liberate monomeric sugars (glucose and xylose) for downstream fermentation, enzymatic saccharification of this material was performed using a cocktail of cellulase and endoxylanase enzymes tailored for hydrolysis of lignocellulosic biomass. As expected, pretreatment with [C$_2$mim][OAc] provided >90% of the theoretical glucose and >70% of the theoretical xylose yields after a 24 hr incubation with enzymes. Based on the compositional analysis it was not surprising that [Van][H$_2$PO$_4$] gave only 50% glucose and <40% xylose yields at this time point.

Figure 13:
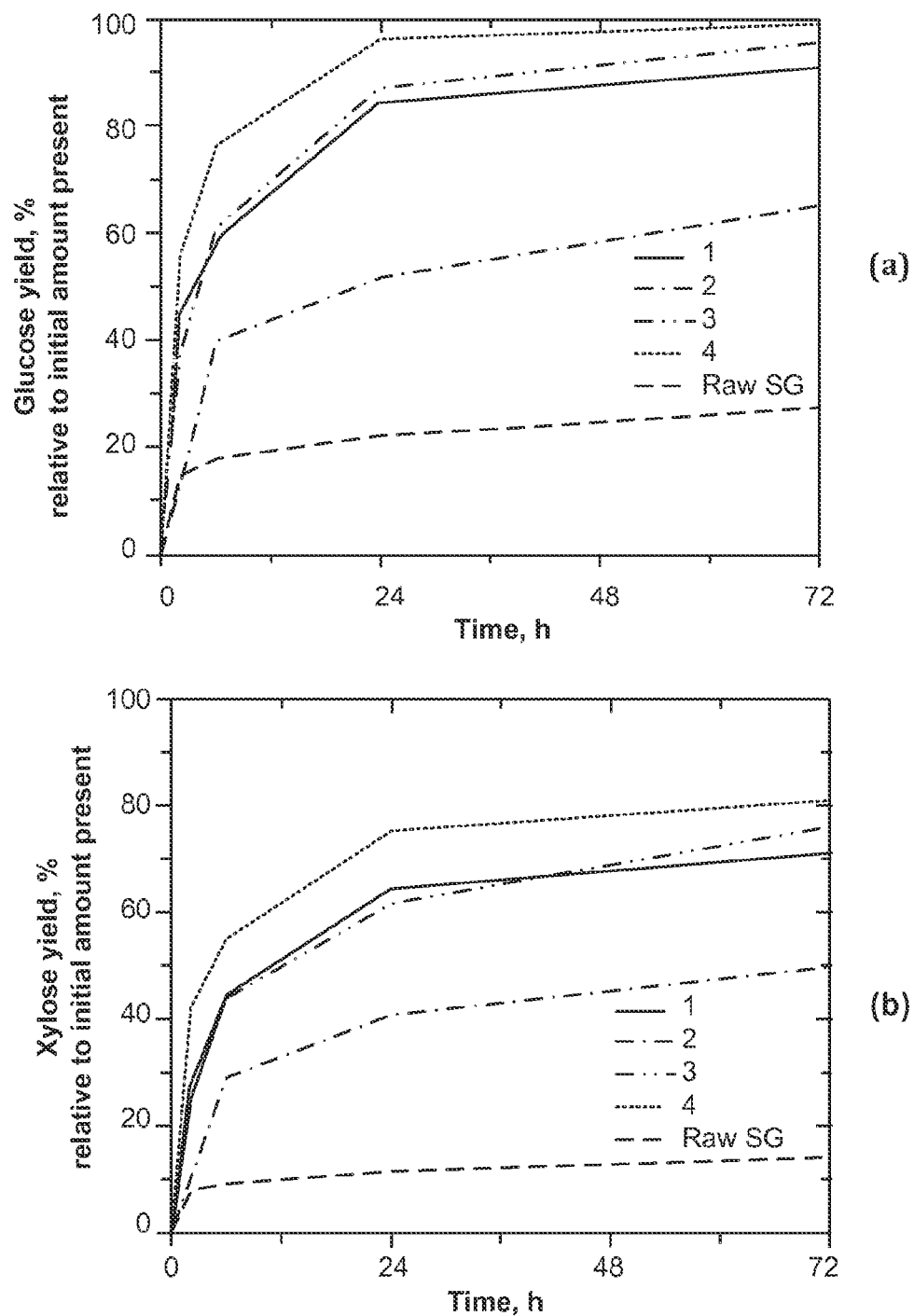
FIG. 13 depicts yields of glucose (a) and xylose (b) from raw switchgrass (SG) and SG pretreated with [Fur][H$_2$PO$_4$] (1), [Van][H$_2$PO$_4$] (2), [p-Anis][H$_2$PO$_4$] (3) and [C$_2$mim][OAc](4).

Pretreatment with ILs [Fur][H$_2$PO$_4$] and [p-Anis][H$_2$PO$_4$] gave >80% glucose and approximately 60% xylose yields after the 24 hr incubation period, and when the reaction was extended to 72 hr, both compounds provided 90-95% glucose and 70-75% xylose yields. Under these conditions, the ILs [Fur][H$_2$PO$_4$] and [p-Anis][H$_2$PO$_4$] compared very well to the benchmark IL, [C$_2$mim][OAc](FIG. 13).

Computational Analysis of ILs:

Kamlet-Taft solvent parameters have been used to measure the ability of a solvent to donate a hydrogen bond ($\alpha$), and accept a hydrogen bond ($\beta$) (45). It has been shown that anion basicity ($\beta$) correlates with the ability of an IL to dissolve lignocellulose (46). Net basicity has been reported to be another good indicator of an IL's ability to dissolve cellulose (47, 48), it was demonstrated that net basicity is more effective than $\beta$. A recent experimental study on a range of cations of the same anion combinations demonstrated that cation acidity is also important for cellulose dissolution (49). In the case of ILs [Van][H$_2$PO$_4$] and [p-Anis][H$_2$PO$_4$], one would expect the differential substitution of the electron donating groups to affect the N atom's affinity for the H$_3$PO$_4$ proton. Molecular modeling was performed to estimate these effects.

Figure 14:
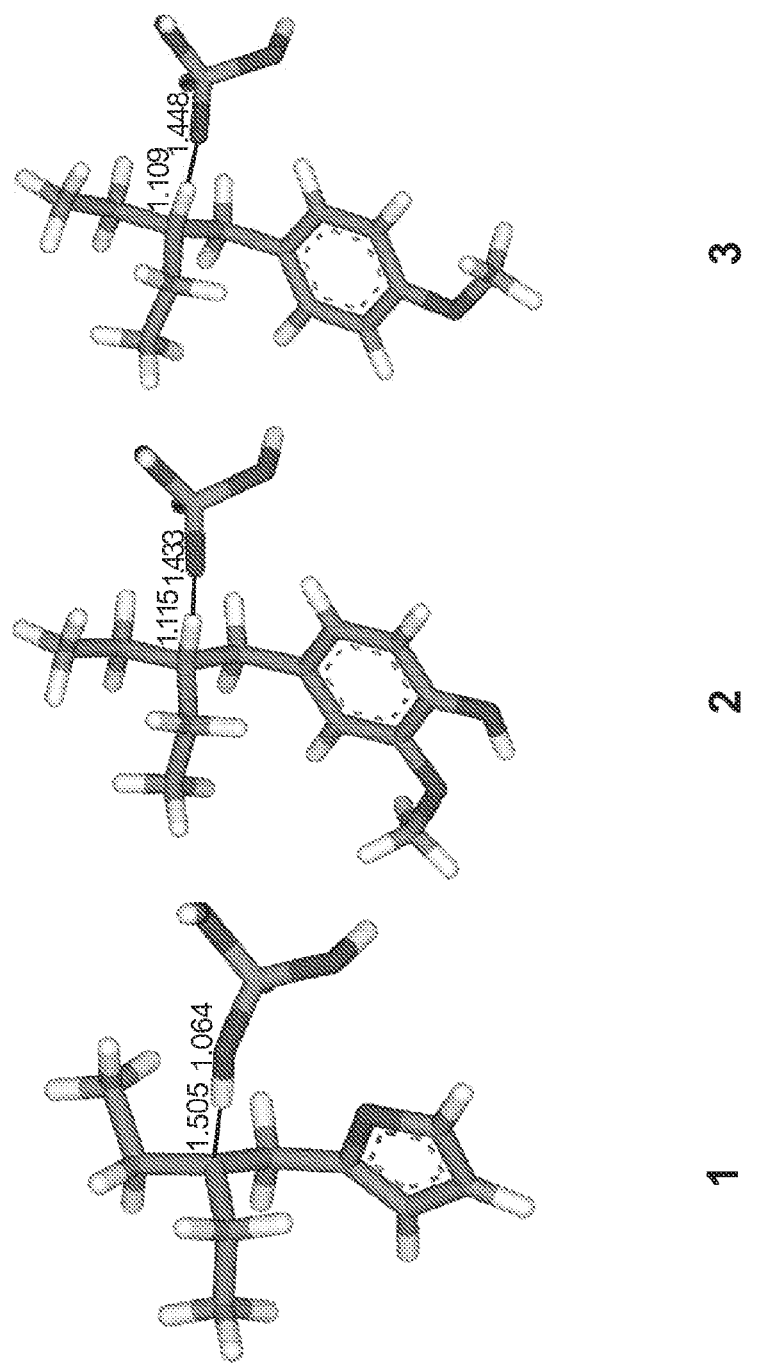
FIG. 14 depicts optimized geometries of [Fur][H2PO4] (1), [Van][H2PO4.] (2) and [p-Anis][H2PO4] (3) ionic liquids.

Table 3 shows the calculated interaction energies (IEs) corrected with basis set super position error correction and IL solvent parameters for ILs investigated here. The IEs for lignin derived ILs are considerably higher in energy than [C$_2$mim][OAc]. Notably, all three biomass derived ILs also have higher $\beta$ values as compared to [C$_2$mim][OAc]. The optimized geometries of ILs from biomass derived aromatic aldehydes are shown in FIG. 14. In general, it can be seen from the IL geometries that the most stable conformation for the interactions are the anion oxygens interacting with hydrogen atom of cation nitrogen. Elongation of N—H bond (from 1.1-1.5 Å) is noted in comparison with the isolated cation N—H bond distance (1.03 Å). Due to the significant elongation of the N—H bond in [Fur][H$_2$PO$_4$], the hydrogen atom migrates and is bound to the oxygen atom of the anion, which allows strong intermolecular interactions.

TABLE 3

Computed Interaction Energy, Proton Affinity, Acidity($\alpha$), Basicity ($\beta$), and Net Basicity of ILs Evaluated in this Study

| Compound | Interaction Energy (kcal/mol) | Proton Affinity (base) (kcal/mol) | $\alpha$ (eV) | $\beta$ (eV) | Net Basicity |
|---|---|---|---|---|---|
| [Fur][H$_2$PO$_4$] | 165.51 | 233 | 2.14 | 3.53 | 1.39 |
| [Van][H$_2$PO$_4$] | 118.14 | 234 | 2.35 | 2.99 | 0.63 |
| [p-Anis][H$_2$PO$_4$]) | 117.83 | 235 | 2.24 | 3.37 | 1.13 |
| [C$_2$mim][OAc] | 106.42 | 257 | 2.28 | 2.97 | 0.69 |

Presence of a para hydroxyl group and a meta methoxyl groups in [Van][H$_2$PO$_4$] versus a para methoxyl group in [p-Anis][H$_2$PO$_4$], showed only slight differences in IEs and proton affinities, but significantly influenced the calculated solvent parameters. Comparison of the experimental results with the calculations of Kamlet-Taft solvent parameters of these ILs show that effective pretreatment requires an IL with high hydrogen bond basicity and high net basicity. From Table 3, it can be seen that net basicity of ILs

[Fur][H₂PO₄] and [p-Anis][H₂PO₄] are higher than that of [C₂mim][OAc]. The higher hydrogen bonding basicity of IL tends to have additional hydrogen bonding interactions between hydroxyl groups of cellulose; hence these ILs could enhance biomass solvation. Combined, the compositional analysis and computational data from biomass-derived ILs containing [H₂PO₄] anions suggests that high basicity and high net basicity are can be required for efficient pretreatment.

Glycome Profiling of Raw and IL Pretreated Switchgrass:

Glycome profiling of raw SG, and switchgrass pretreated with [Fur][H₂PO₄], [p-Anis][H₂PO₄] and [C₂mim][OAc] was conducted to monitor changes in the overall composition and extractability of most major non-cellulosic plant cell wall glycans. This method of analysis was performed to differentiate specific changes to biomass cell walls, and correlate those changes with reduced recalcitrance as a function of pretreatment.

Figure 15A:
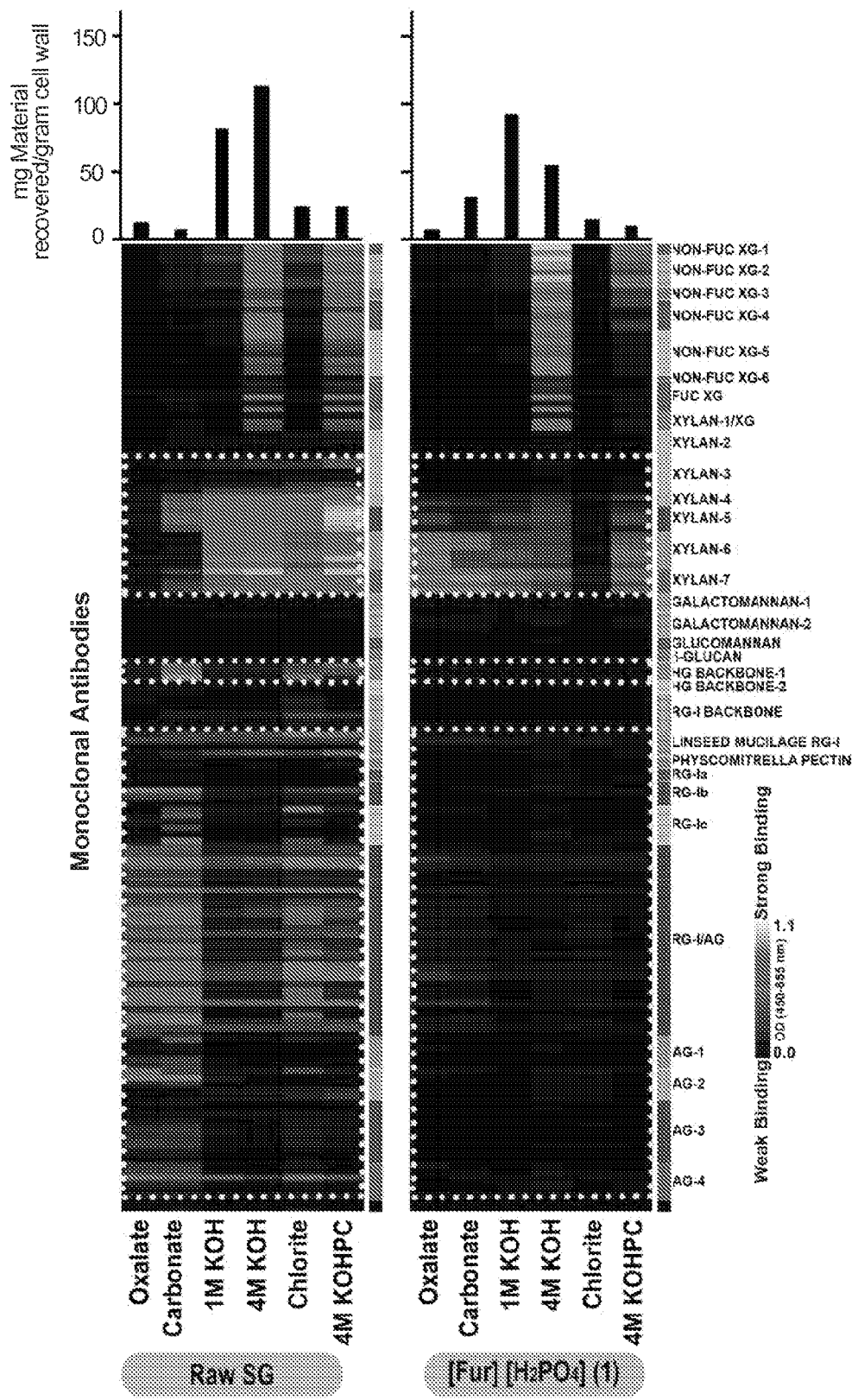
FIG. 15 depicts the results of glycome profiling of raw switchgrass (SG), and SG pretreated with ionic liquids [Fur][H$_2$PO$_4$], [p-Anis][H$_2$PO$_4$] and [C$_2$mim][OAc]: Sequential cell wall extracts (bottom) were subjected to ELISA screens with monoclonal antibodies for most major non-cellulosic plant glycan classes (right). The ELISA binding response values are represented as a color-coded "heatmap" (center) and the recovered masses of carbohydrate material resulting from each extraction step is represented with bar graphs (top).
Figure 15B:
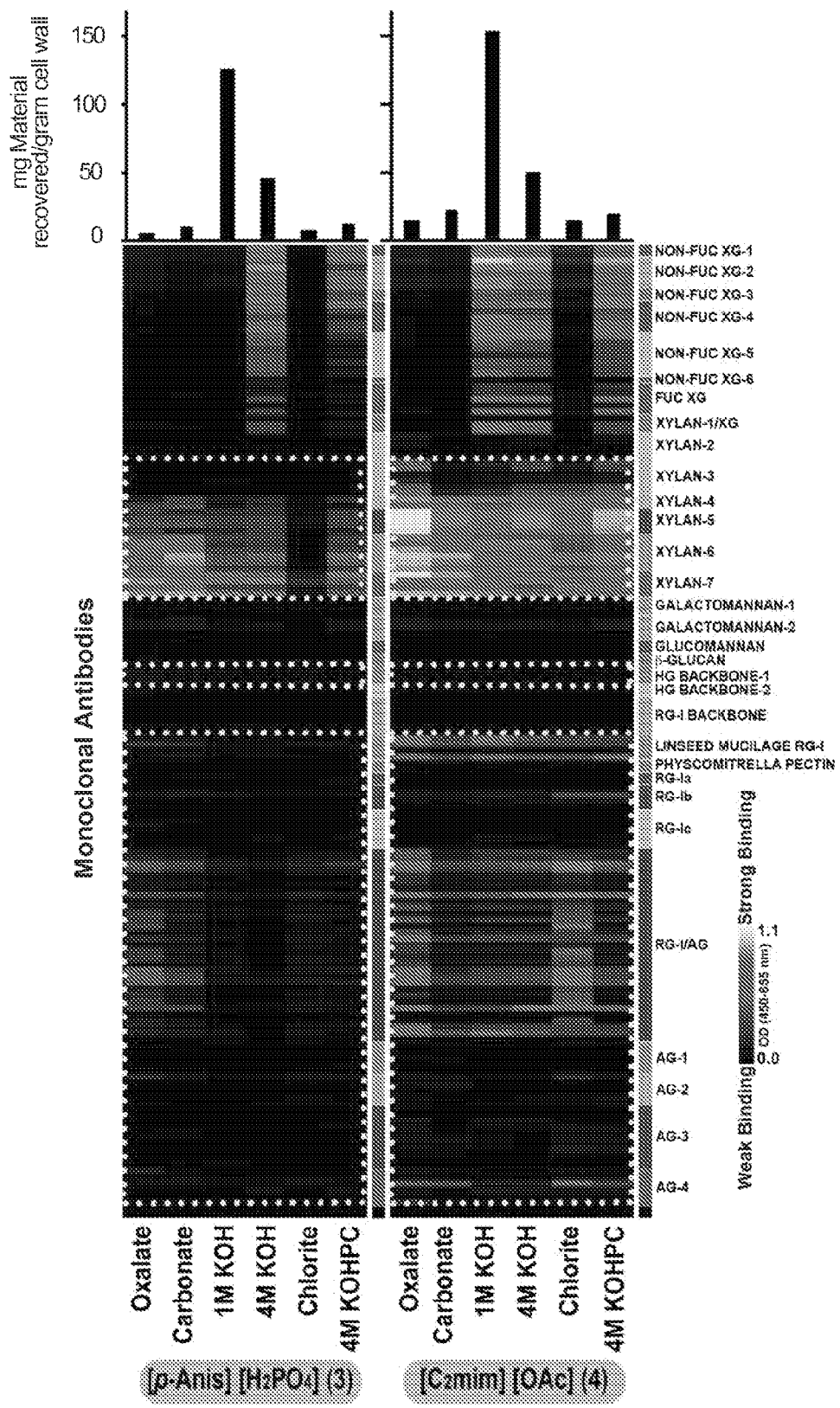

FIG. 15 shows glycome profiles of raw and IL pretreated switchgrass. The glycome profiles of the IL pretreated switchgrass differed significantly from raw untreated switchgrass, emphasizing an overall change in the cell wall structure and integrity due to the solubilization and removal of lignin and lignin-associated carbohydrates during the pretreatment. The major changes in the profiles are highlighted as dotted rectangles. Oxalate and carbonate extracts of all three IL pretreated samples showed significantly greater abundance of unsubstituted homoxylan and/or substituted arabinoxylan epitopes. This is particularly indicated by the higher binding of xylan-6 through 7 groups of McAbs in the case of [Fur][H₂PO₄] and [p-Anis][H₂PO₄] and of xylan-3 through 7 groups of McAbs in in the case of SG pretreated with [C₂mim][OAc]. A marginal increase in the amount of carbohydrate materials recovered in the carbonate extracts was observed in the case of biomass pretreated with [Fur][H₂PO₄] and [C₂mim][OAc]. In all IL pretreated samples, relatively higher amounts of carbohydrate materials were released in 1M KOH extracts compared to the untreated biomass. Correspondingly, notable reductions were observed in all IL pretreated samples in terms of the amount of carbohydrates extracted with 4M KOH. These results clearly demonstrate enhanced extractability of hemicellulosic glycans in IL pretreated samples. Earlier studies have shown that such increased hemicellulose extractability (particularly xylan) is clearly indicative of reduced recalcitrance (50). Enhanced extractability of xyloglucan (XG) epitopes was observed in SG pretreated with [C₂mim][OAc]. In these samples, epitopes recognized by nearly all XG groups of McAbs were abundantly present in 1 M KOH extracts in addition to 4M KOH and 4MKOH PC extracts. Homogalacturonan epitopes (recognized by HG Backbone-1 group of McAbs) representing pectic backbone sugars were completely removed in all extracts of SG pretreated with all ILs. Pectic-arabinogalactan epitopes (as indicated by the binding of RG-I/AG and AG 1 through 4 groups of McAbs) were present in significant proportions in oxalate, carbonate, chlorite and 4MKOH PC extracts of raw SG biomass samples. Interestingly, in [Fur][H₂PO₄] and [p-Anis][H₂PO₄] pretreated samples, there was a significant reduction in the abundance of these pectic-arabinogalactan epitopes further emphasizing an overall change in the cell wall structure and integrity during these IL pretreatments. The significant reduction observed in the binding intensities of pectic-arabinogalactan directed McAbs in [Fur][H₂PO₄] and [p-Anis][H₂PO₄] pretreated biomass samples, may be due to two possible reasons. Firstly, pretreatment conditions facilitated the removal of epitope structures from the corresponding glycans and secondly, pretreatment caused significant shortening these cell wall glycans making their adsorption to the ELISA plates inefficient. It is also possible that a combination of these effects occurred. In contrast, [C₂mim][OAc] pretreated SG still contained pectic-arabinogalactan epitopes, most notability in oxalate and chlorite extracts, suggesting a mechanism of action between [Fur][H₂PO₄] and [p-Anis][H₂PO₄] that differs from that of [C₂mim][OAc].

Effect of IL-Pretreatment on Lignin-Carbohydrate Associations:

Treatment of plant cell walls with chlorite cleaves and removes lignin, extracting all lignin-associated polysaccharides. The chlorite extracts from samples pretreated with [Fur][H₂PO₄] and [p-Anis][H₂PO₄] were virtually devoid of all glycan epitopes, suggesting a significant reduction in lignin-polysaccharide associations in SG subjected to pretreatment with these ILs. In contrast, the chlorite extracts from [C₂mim][OAc] pretreated SG, however, still contained significant amounts of xylans and pectic-arabiogalactans. Compositional analysis revealed that [C₂mim][OAc] removes greater amounts of lignin (52.4%) as compared to [Fur][H₂PO₄] (20.0%) and [p-Anis][H₂PO₄] (43.0%), suggesting that SG pretreated with [C₂mim][OAc] may retain polysaccharides through cell wall associations. There seems to be no such associations between lignin and xyloglucans in any of the ILs tested. Taken together, the above results indicate that both [Fur][H₂PO₄] and [p-Anis][H₂PO₄] reduce biomass recalcitrance through a similar mechanism, one that may be significantly distinct from that of [C₂mim][OAc].

Cost Estimates of Biomass-Derived ILs:

One important consideration for the proposed application for any ionic liquid is cost. Replacement of diethylamine and Na(OAc)₃BH with NH₃ and H₂ for reductive amination (51) could significantly lower the cost of the production of ionic liquid and/or other products from lignocellulosic biomass (e.g., biofuel) to $4/kg, $4/gal, or less. These results indicate that this approach to the production of renewable ionic liquids holds significant promise.

III. Conclusions

We have shown the first synthesis and evaluation of a series of ionic liquids from monomers obtained from lignin and hemicellulose. Reductive amination of these aromatic aldehydes followed by treatment with phosphoric acid provided three ionic liquids in excellent yields without the need for chromatographic purification. Compositional analysis and sugar yields from enzymatic hydrolysis of pretreated switchgrass was used to compare these biomass-derived ILs to [C₂mim][OAc]. Molecular modeling provided insight of IL interaction with biomass and showed a clear trend of IL performance based on IEs. Enzymatic saccharification with [Fur][H₂PO₄] and [p-Anis][H₂PO₄] provided 90% and 96% of total possible glucose and 70% and 76% of total possible xylose, respectively, after biomass pretreatment. As expected, these ILs also showed high β values, high net basicity and good ability to remove lignin. Computationally, [Van][H₂PO₄] showed the lowest net basicity, and lower lignin removal efficiency and low sugar yields were observed experimentally. We found that [Fur][H₂PO₄] and [p-Anis][H₂PO₄] had higher β values and higher net basicity than [C₂mim][OAc]. Though [Fur][H₂PO₄] and [p-Anis][H₂PO₄] were slightly less effective towards lignin removal, sugar yields from SG pretreated with these compounds were nearly equivalent to yields from SG pretreated with [C₂mim]

[OAc]. Glycome profiling experiments suggest that the biomass derived ILs [Fur][H$_2$PO$_4$] and [p-Anis][H$_2$PO$_4$] act on plant cell walls in a mechanism distinct from [C$_2$mim][OAc], and studies are underway to understand these process implications in terms of lignin and hemicellulose depolymerization and IL recycling. These results indicate that biomass derived renewable ionic liquids are very effective in pretreating biomass and other industrial applications.

IV. Experimental Section

All solvents and chemicals were reagent grade and used without purification. NMR spectra were obtained on an Anasazi Eft-90 instrument (90 MHz for $^1$H) in DMSO-d$_6$ and calibrated with TMS for $^1$H ($\delta$=0.00 ppm) and DMSO for $^{13}$C ($\delta$=39.5 ppm), respectively. Mass spectra were obtained on an Agilent 6890 GC equipped with an Agilent 5973 mass detector. Synthetic reactions were performed in triplicate and average yields are reported.

Reductive Amination of Aldehydes to Tertiary Amines:

N-ethyl-N-(furan-2-ylmethyl)ethanamine

To a solution of furfural (10.0 g, 104 mmol, 1 equiv.) in 1,2-dichloroethane (360 mL), cooled to 0° C., was added diethylamine (18.3 g, 121 mmol, 1.2 equiv.) and allowed to stir for 15 min. Sodium triacetoxyborohydride (30.9 g, 1.4 equiv.) was added portion-wise, and the mixture was stirred allowed to warm to room temperature overnight under N$_2$. The solution was quenched by adding aq. 3M HCl and the amine product was thus drawn in the aqueous phase (pH~1). The organic impurities were removed with the dichloroethane phase, and the aqueous phase was washed with CH$_2$Cl$_2$. The pH of the aqueous phase was raised to 9.5 by addition of 3M KOH, and the product was extracted 2× with EtOAc. The combined organic layers are dried over Na$_2$SO$_4$, and concentrated to afford the product (13.1 g, 82% yield). All of the tertiary amine products below were prepared using this method. m/z [M+] Obsd. 153.1 Calcd. 153.12 for C$_9$H$_{17}$NO; $^1$H NMR: 0.99 (t, 6H, J=8 Hz), 2.41 (q, 4H, J=8 Hz), 3.56 (s, 2H), 6.23 (m, 1H) 6.34 (m, 1H) 7.51 (m, 1H); $^{13}$C NMR: 11.9 (2C), 46.3 (2C), 48.3, 107.9, 109.9, 141.8, 152.7.

4-((diethylamino)methyl)-2-methoxyphenol

Following the general protocol for the reductive amination of aldehydes to tertiary amines, 15.0 g (100 mmol, 1 eq) of vanillin yielded the desired product (18.3 g, 89% yield). m/z [M$^+$] Obsd. 209.1 Calcd. 209.14 for C$_{12}$H$_{19}$NO$_2$; $^1$H NMR: 0.96 (t, 6H, J=8 Hz), 2.43 (q, 4H, J=8 Hz), 3.41 (s, 2H), 3.74 (s, 3H), 6.70 (s, 2H), 6.85 (s, 1H); $^{13}$C NMR: 11.6 (2C), 46.0 (2C), 55.5, 56.9, 112.6, 115.1, 120.9, 130.6, 145.3, 147.4.

N-ethyl-N-(4-methoxybenzyl)ethanamine

Following the general protocol for the reductive amination of aldehydes to tertiary amines, with 14.0 g (103 mmol, 1 eq) of p-anisaldehyde, yielded the desired product (19.0 g, 96% yield). m/z [M$^+$] Obsd. 193.1 Calcd. 193.15 for C$_{15}$H$_{19}$NO; $^1$H NMR: 0.96 (t, 6H, J=8 Hz), 2.43 (q, 4H, J=8 Hz), 3.44 (s, 2H), 3.73 (s, 3H) 6.85 (d, $_{2H}$, J=9 Hz), 7.22 (d, 2H, J=9 Hz); $^{13}$C NMR: 11.6 (2C), 45.9 (2C), 54.8, 56.3, 113.3 (2C), 129.5 (2C), 131.6, 158.2.

Formation of Ionic Liquids with Phosphoric Acid:

N-ethyl-N-(furan-2-ylmethyl)ethanamine, H$_3$PO$_4$ salt ([Fur][H$_2$PO$_4$])

To a stirred 2M solution of N-ethyl-N-(furan-2-ylmethyl) ethanamine (10.0 g, 65.0 mmol, 1 equiv.) in MeOH (32.6 mL) at 0° C. was slowly added H$_3$PO$_4$ (6.4 g, 65.0 mmol, 1 equiv.). The solution was allowed to stir, warming to room temperature for 3 h. Methanol was evaporated under vacuum and the ionic liquid 1 was obtained (16.0 g, 98% yield). All of the dihydrogen phosphate ionic liquids described below were prepared by this method. $^1$H NMR: 1.19 (t, 6H, J=8 Hz), 2.79 (q, 4H, J=8 Hz), 4.09 (s, 2H), 6.49 (m, 1H) 6.65 (m, 1H), 7.69 (m, 1H); $^{13}$C NMR: 9.74 (2C), 46.4 (2C), 48.8, 111.1, 112.9, 144.2, 146.4.

4-((diethylamino)methyl)-2-methoxyphenol, H$_3$PO$_4$ salt ([Van][H$_2$PO$_4$])

To a stirred 2M solution of 4-((diethylamino)methyl)-2-methoxyphenol (10.0 g, 48.0 mmol, 1 equiv.) in MeOH (23.9 mL) at 0° C. was slowly added H$_3$PO$_4$ (4.68 g, 48.0 mmol, 1 equiv.). The solution was allowed to stir, warming to room temperature for 3 h. Methanol was evaporated under vacuum and the ionic liquid 2 was obtained (14.4 g, 98% yield). $^1$H NMR: 1.09 (t, 6H, J=8 Hz), 2.70 (q, 4H, J=8 Hz), 3.74 (s, 2H), 3.78 (s, 3H), 6.78 (s, 2H), 7.07 (s, 1H); $^{13}$C NMR: 9.08 (2C), 45.2 (2C), 55.3, 55.9, 114.4, 115.5, 123.3 (2C), 147.2, 147.8.

N-ethyl-N-(4-methoxybenzyl)ethanamine, H$_3$PO$_4$ salt ([p-Anis][H$_2$PO$_4$])

To a stirred 2M solution of N-ethyl-N-(4-methoxybenzyl) ethanamine (10.0 g, 52.0 mmol, 1 equiv.) in MeOH (25.9 mL) at 0° C. was slowly added H$_3$PO$_4$ (5.07 g, 52.0 mmol, 1 equiv.). The solution was allowed to stir, warming to room temperature for 3 h. Methanol was evaporated under vacuum and the ionic liquid 3 was obtained (14.9 g, 99% yield). $^1$H NMR: 1.18 (t, 6H, J=8 Hz), 2.85 (q, 4H, J=8 Hz), 3.77 (s, 3H), 4.00 (s, 2H), 6.95 (d, 1H, J=10 Hz), 7.52 (d, 2H, J=8 Hz); $^{13}$C NMR: 9.1 (2C), 45.3, 48.8, 54.6, 55.2, 114.1 (2C), 124.7, 132.1 (2C), 160.0.

Pretreatment Conditions:

400 milligrams of dry switchgrass were mixed with 3.6 grams of ILs (10% water) to give a 10 wt % biomass loading in tubular reactors made of 0.75 inch diameter×6 inch length stainless steel (SS316) tubes and sealed with stainless steel caps. All pretreatment reactions were run in triplicate. Tubular reactors were heated to reaction temperature (160° C.) in convention oven. The heat up time was ~10 min and is not included in the stated reaction times. After pretreatment, the reactors were allowed to cool to room temperature. The mixture of IL, water, and pretreated biomass was transferred to a 50 mL falcon tube using DI water to a final volume of 25 mL and then centrifuged at 3220 rcf to separate the solid and liquid phases. An aliquot of supernatant was taken for lignin and sugar analysis. The solid fraction was washed sequentially with 40 mL of hot water, 40 mL of 1:1 acetone:water, and three times with 40 mL of hot water to remove any residual IL and/or sugars. Washed solids were lyophilized in a FreeZone Freeze Dry System (Labconco, Kansas City, Mo.) for composition analysis and enzymatic saccharification.

Enzymatic Saccharification:

Enzymatic saccharification of untreated and pretreated samples were run in triplicate following NREL LAP 9 "Enzymatic Saccharification of Lignocellulosic Biomass" standard conditions (50° C., 0.05 M citrate buffer, pH 4.8) (52). Citrate buffer (final molarity 50 mM), sodium azide (antimicrobial, final concentration of 0.02 g/L), enzymes, and DI water were mixed with pretreated solids to achieve a final solid loading of ~10%. Enzyme loadings of 15 mg Ctec2/g untreated biomass supplemented with 1.5 mg Htec2/g glucan. An aliquot of supernatant was taken at 2, 6, 24, and 72 h and was analyzed by HPLC for monosaccharide content as described previously (53). Glucose yield was calculated from the maximum potential glucose available from glucan in pretreated biomass.

Glycome Profiling:

To conduct glycome profiling, alcohol insoluble residues of cell walls derived from raw and IL pretreated SG were subjected to sequential extractions using increasingly harsh reagents (54). In the case of native plant cell walls, mild conditions such as oxalate and carbonate extracts, remove the most loosely bound pectic polysaccharides. Alkaline treatment with 1M KOH removes more tightly bound pectin and hemicelluloses that mainly comprise xylan and pectin, and 4M KOH extracts xyloglucans in addition to xylan and pectins. Treatment with acetic acid/chlorite at high temperature (chlorite extraction) breaks down most of the lignin, releasing lignin-associated polysaccharides into this fraction. Finally, a 4M KOHPC treatment removes any residual polysaccharides that remain bound to the cell wall via association with lignin. To facilitate glycome profiling, all extracts were probed with a comprehensive suite of cell wall glycan directed monoclonal antibodies (McAbs), and the binding responses of these McAbs are represented as color-coded "heat maps" (54). The total amounts of carbohydrates recovered under each extraction condition were also quantified gravimetrically, and are represented as bar graphs atop FIG. 15.

V. References

1. Welton T (1999) Room temperature ionic liquids. Solvents for synthesis and catalysis. *Chem Rev* 99(8):2071-2083.
2. Brennecke J & Maginn E (2001) Ionic liquids: Innovative fluids for chemical processing. *AIChE J* 47(11):2384-2389.
3. Giernoth R (2007) Homogeneous catalysis in ionic liquids. *Top Curr Chem* 276:1-23.
4. Stoimenovski J, MacFarlane D R, Bica K, & Rogers R D (2010) Crystalline vs. ionic liquid salt forms of active pharmaceutical agents: A position paper. *Pharm Res* 27(4):521-526.
5. Bermúdez M D, Jiménez A E, Sanes J, & Carrión F J (2009) Ionic liquids as advanced fluid lubricants. *Molecules* 14(8):2888-2908.
6. Galiński M, Lewandowski A, & Stgpniak I (2006) Ionic liquids as electrolytes. *Electrochim Acta* 51(26):5567-5580.
7. Lewandowski A & Swiderska-Mocek A (2009) Ionic Liquids as electrolytes for Li-ion batteries—An overview of electrochemical studies, *J Power Sources* 194(2):601-609.
8. Park J W, Ueno K, Tachikawa N, Dokko K, & Wantanabe M (2013) Ionic liquid electrolytes for lithium-sulfur batteries. *J Phys Chem C* 117(40):20531-20541.
9. Mills D (2004) Advances in solar thermal electricity technology. *Sol Energy* 76:19-31.
10. Shannon M S & Bara J E (2011) Reactive and reversible ionic liquids for CO2 capture and acid gas removal. *Sep Sci Technol* 47(2):178-188.
11. Fauzi A H M & Amin N A S (2012) An overview of ionic liquids as solvents in biodiesel synthesis. *Renewable and Sustainable Energy Reviews* 16:5770-5786.
12. Stark A (2011) Ionic liquids in the biorefinery: a critical assessment of their potential. *Energy Environ Sci* 4:19-32.
13. Bokinski G, et al. (2011) Synthesis of three advanced biofuels from ionic-liquid pretreated switchgrass using engineered *Escherichia coli*. *Proc Natl Acad Sci USA* 108(50): 19949-19954.
14. Li C, et al. (2010) Comparison of dilute acid and ionic liquid pretreatment of switchgrass: Biomass recalcitrance, delignification and enzymatic saccharification. *Bioresour Technol* 101(13):4900-4906.
15. Shi J, et al. (2012) Impact of mixed feedstocks and feedstock densification on ionic liquid pretreatment efficiency. *Biofuels* 4(1):63-72.
16. Simmons B A, Loque D, & Blanch H W (2008) Next-generation biomass feedstocks for biofuel production. *Genome Biol* 9(12):1-6.
17. Kilpeläinen A, et al. (2003) Wood properties of Scots pines (*Pinus sylvestris*) grown at elevated temperature and carbon dioxide concentration. *Tree Physiol* 23(13):889-897.
18. Perez-Pimienta J A, et al. (2013) Comparison of the impact of ionic liquid pretreatment on recalcitrance of agave bagasse and switchgrass. *Bioresour Technol* 127: 18-24.
19. Kostianinen K. et al. (2008) Wood properties of trembling aspen and paper birch after 5 years of exposure to elevated concentrations of CO2 and O3. *Tree Physiol* 28:805-813.
20. Schädel C, Blöchl A, Richter A, & Günter H (2010) Quantification and monosaccharide composition of hemicelluloses from different plant functional types. *Plant Physiol Biochem* 48(1): 1-8.
21. Mosier N, et al. (2005) Features of promising technologies for pretreatment of lignocellulosic biomass. *Biores Technol* 96:673-686.
22. Wyman C. et al. (2005) Coordinated development of leading biomass pretreatment technologies. *Biores Technol* 96:1959-1966.
23. Palmqvist E & Hahn-Hägerdal B (2000) Fermentation of lignocellulosic hydrolysates I: Inhibition and detoxification. *Biores Technol* 74:17-24.
24. Pu Y, Jiang N, & Ragauskas A J (2007) Ionic liquid as a green solvent for lignin. *J Wood Chem Technol* 27(1): 23-33.
25. Binder J B & Raines R T (2009) Simple chemical transformations of lignocellulosic biomass into furans for fuels and chemicals. *J Am Chem Soc* 131(5): 1979-1985.
26. Lee S H, Doherty T V, Linhardt R J, & Dordick J S (2008) Ionic liquid-mediated selective extraction of lignin from wood leading to enhanced enzymatic cellulose hydrolysis. *Biotechnol Bioeng* 102(5):1368-1376.
27. Ebel K, Koehler H, Gamer A O, & Jäckh R (2012) Imidazole and derivatives: Section 4.1—The Radziszewski Reaction. in *Ullmann's Encyclopedia of Industrial Chemistry*, pp 638-639.
28. Kirk R E & Othmer D F (2005) in *Kirk-Othmer Encyclopedia of Chemical Technology* eds Kroschwitz J I & Seidel A (Wiley), p 16.

29. Kilpelainen I, et al. (2007) Dissolution of wood in ionic liquids. *J Agric Food Chem* 55(22):9142-9148.
30. Singh S, Simmons B, & Vogel K (2009) Visualization of biomass solubilization and cellulose regeneration during ionic liquid pretreatment of switchgrass. *Biotechnol Bioeng* 104(1):68-75.
31. Pandey M P & Kim C S (2011) Lignin depolymerization and conversion: A review of thermochemical methods. *Chem Eng Technol* 34(1):29-41.
32. Kleen M & Gellerstedt G (1991) Characterization of chemical and mechanical pulps by pyrolysis-gas chromatography/mass spectrometry. *J Anal Appl Pyrolysis* 19:139-152.
33. Xiang Q & Lee Y Y (2000) Oxidative cracking of precipitated hardwood lignin by hydrogen peroxide. *Appl Biochem Biotechnol* 84-86(1-9):153-162.
34. Pearl I A (1942) Vanillin from lignin materials. *J Am Chem Soc* 64(6):1429-1431.
35. Liu S, et al. (2013) Process of lignin oxidation in ionic liquids coupled with separation. *RSC Adv* 3(17):5789-5793.
36. Gutiérrez A, Caramelo L, Prieto A, Martinez M J, & Martinez A T (1994) Anisaldehyde production and arylalcohol oxidase and dehydrogenase activities in lignolytic fungi of the genus *Pleurotus*. *Appl Environ Microbiol* 60(6):1783-1788.
37. Binder J B. Gray M J, White J F, Zhang Z C, & Holladay J E (2009) Reactions of lignin model compounds in ionic liquids. *Biomass Bioenergy* 33:1122-1130.
38. Abdel-Magid A F, Carson K G. Harris B D, Maryanoff C A, & Shah R D (1996) Reductive amination of aldehydes and ketones with sodium triacetoxyborohydride. studies on direct and indirect reductive amination procedures. *J Org Chem* 61(11):3849-3862.
39. Pretsch E, Bühlmann P, & Affolter C (2000) Structure Determination of Organic Compounds. (Springer, Berlin), pp 121-122, 208.
40. Sun N, et al. (2014) Understanding pretreatment efficacy of four cholinium and imidazolium ionic liquids by chemistry and computation. *Green Chem.*
41. Brandt A, J G, Hallett J. & Welton T (2013) Deconstruction of lignocellulosic biomass with ionic liquids. *Green Chem* 15:550-583.
42. Fukaya Y, Hayashi K, Wada M, & Ohno H (2008) Cellulose dissolution with polar ionic liquids under mild conditions: required factors for anions. *Green Chem* 10(1):44-46.
43. Ohno H & Fukaya Y (2009) Task specific ionic liquids for cellulose technology. *Chem Lett* 38(1):2-7.
44. Samuel R, Foston M, Jiang N, Allison L, & Ragauskas A J (2011) Structural changes in switchgrass lignin and hemicelluloses during pretreatments by NMR analysis. *Polym Degrad Stab* 96(11):2002-2009.
45. Kamlet M, Abboud J, & Taft R (1977) The solvatochromic comparison method. 6. The .pi.* scale of solvent polarities. *J Am Chem Soc* 99(18):6027-6038.
46. Brandt A, Hallett J P, Leak D J, Murphy R J, & Welton T (2010) The effect of the ionic liquid anion in the pretreatment of pine wood chips. *Green Chem* 12(4):672-679.
47. Hauru L K J, Hummel M, King A W T, Kilpeliainen I A, & Sixta H (2012) Role of solvent parameters in the regeneration of cellulose from ionic liquid solutions. *Biomacromolecules* 13(9):2896-2905.
48. Parviainen A, et al. (2013) Predicting cellulose solvating capabilities of acid-base conjugate ionic liquids. *Chem Sus Chem* 6(11):2161-2169.
49. King A W T, et al. (2012) Relative and inherent reactivities of imidazolium-based ionic liquids: the implications for lignocellulose processing applications. *RSC Adv* 2(21):8020-8026.
50. Pattathil S, el al. (2012) Changes in cell wall carbohydrate extractability are correlated with reduced recalcitrance of HCT downregulated alfalfa biomass. *Ind Biotechnol* 8(4): 217-221.
51. Gomez S, Peters J O. & Maschmeyer T (2002) The reductive amination of aldehydes and ketones and the hydrogenation of nitriles: Mechanistic aspects and selectivity control. *Adv. Synth. Catal.* 344(10): 1037-1057.
52. Sluiter A H B, Ruiz R, Scarlata C, Sluiter J, Templeton D: (2005) *Determination of structural carbohydrates and lignin in biomass* (National Renewable Energy Laboratory), (Program B).
53. Shi J. et al. (2013) One-pot ionic liquid pretreatment and saccharification of switchgrass. *Green Chem.*
54. Pattathil S, Avci U, & Hahn M G (2012) Immunological approaches to plant cell wall and biomass characterization: glycome profiling. *Methods Mol Biol* 908:61-72.

The invention has been described by way of illustration, and not by limitation. It is to be understood that the particular embodiments depicted in the figures and the terminology which has been used has been intended in a nature of words of description rather than of limitation. It is to be further understood that any combination of the solvents and compositions described in the foregoing paragraphs are deemed to be encompassed by the appended claims. It is to be further understood that all specific embodiments of the method of lignin extraction and biomass treatment are deemed to be encompassed by the appended claims. Many modifications and variations of the present invention are possible in light of the above teachings. It is therefore to be understood that the obvious modifications are deemed to be encompassed within the appended claims.

What is claimed is:

1. A method for preparing an ionic liquid comprising:
   contacting a starting material comprising lignin with a depolymerization agent to depolymerize the lignin and form a mixture of aldehyde containing compounds;
   contacting the mixture of aldehyde containing compounds with an amine under conditions suitable to convert the mixture of aldehyde containing compounds to a mixture of amine containing compounds; and
   contacting the mixture of amine containing compounds with an acid under conditions suitable to form an ammonium salt, thereby preparing the ionic liquid, wherein:
   the ionic liquid comprises at least one compound of the following formula:

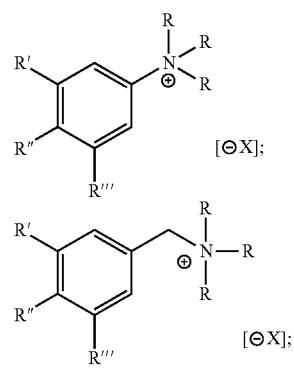

-continued

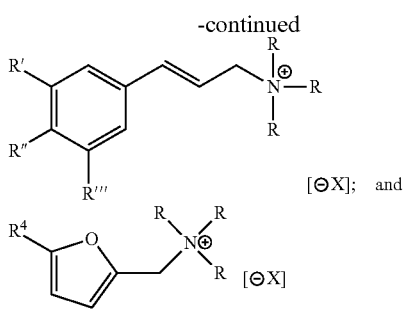

wherein each of the R groups of the nitrogen is independently selected from the group consisting of H, $CH_3$, and $CH_2CH_3$;

at least two of the R groups of the nitrogen are independently selected from the group consisting of $CH_3$, and $CH_2CH_3$;

R', R", and R''' are independently selected from the group consisting of H, OH, and $OCH_3$;

$R^4$ is selected from the group consisting of H, OH, and $CH_2OH$; and

X comprises an acid anion.

2. The method of claim 1, wherein the step of contacting the starting material with a depolymerization agent comprises contacting the starting material with one or more compositions selected from the group consisting of an ionic liquid; hydrogen gas; a hydrogen donating agent selected from the group consisting of tetralin, sodium formate and formic acid; a dilute acid; a concentrated acid; a base; a catalyst and an oxidizing agent selected from the group consisting of nitrobenzene, metal oxides, hydrogen peroxide, and oxygen gas; Fenton's reagent; metal organic frameworks of copper or iron; and ammonium hydroxide.

3. The method of claim 2, wherein the depolymerization agent comprises a lignin-derived ionic liquid.

4. The method of claim 2, wherein the depolymerization agent comprises an imidazolium ionic liquid.

5. The method of claim 1, wherein the step of contacting the mixture of aldehyde containing compounds with an amine is performed under reducing conditions.

6. The method of claim 5, wherein the reducing conditions comprise an amine, a Brønsted acid; and a hydride donating reducing agent.

7. The method of claim 6, wherein the amine is selected from the group consisting of a cyclic amine, an acyclic amine, a monoamine, and a dialkylamine.

8. The method of claim 6, wherein the Brønsted acid is selected from the group consisting of formic acid, acetic acid, proprionic acid, and an aromatic carboxylic acid.

9. The method of claim 6, wherein the reducing agent is selected from the group consisting of sodium triacetoxyborohydride, sodium cyanoborohydride, sodium borohydride-trifluoroacetic acid, hydrogen gas and a catalyst, and polymethylhydrosiloxane (PMHS).

10. The method of claim 1, wherein the step of contacting the mixture of amine containing compounds with an acid under conditions suitable to form an amine salt comprises a salt metathesis reaction, wherein the conditions of the salt metathesis reaction comprise acid in a polar solvent.

11. The method of claim 10, wherein the acid is a mineral acid selected from the group consisting of sulfuric and phosphoric acid.

12. The method of claim 1, wherein the contacting steps are performed in a single reaction vessel.

* * * * *